United States Patent
Stahmann et al.

(10) Patent No.: US 7,938,782 B2
(45) Date of Patent: May 10, 2011

(54) PREDICTION OF DISORDERED BREATHING

(75) Inventors: Jeffrey E. Stahmann, Ramsey, MN (US); John D. Hatlestad, Maplewood, MN (US); Quan Ni, Shoreview, MN (US); Jesse Hartley, Lino Lakes, MN (US); Douglas R. Daum, Oakdale, MN (US); Kent Lee, Fridley, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 223 days.

(21) Appl. No.: 12/152,029

(22) Filed: May 12, 2008

(65) Prior Publication Data
US 2008/0221468 A1 Sep. 11, 2008

Related U.S. Application Data

(63) Continuation of application No. 10/643,016, filed on Aug. 18, 2003, now Pat. No. 7,396,333.

(51) Int. Cl.
*A61B 5/08* (2006.01)

(52) U.S. Cl. ......... 600/536; 600/506; 600/529; 600/547

(58) Field of Classification Search .......... 324/600–727; 600/506, 529–543, 547
See application file for complete search history.

(56) References Cited

U.S. PATENT DOCUMENTS

| | | | |
|---|---|---|---|
| 4,312,734 A | 1/1982 | Nichols | |
| 4,365,636 A | 12/1982 | Barker | |
| 4,390,405 A | 6/1983 | Hahn et al. | |
| 4,562,841 A | 1/1986 | Brockway et al. | |
| 4,702,253 A | 10/1987 | Nappholz et al. | |
| 4,777,962 A | 10/1988 | Watson et al. | |
| 4,784,162 A | 11/1988 | Ricks et al. | |
| 4,802,485 A | 2/1989 | Bowers et al. | |
| 4,813,427 A | 3/1989 | Schlaefke et al. | |
| 4,827,935 A | 5/1989 | Geddes et al. | |
| 4,827,943 A | 5/1989 | Bornn et al. | |
| 4,830,008 A | 5/1989 | Meer | |
| 4,836,219 A | 6/1989 | Hobson et al. | |
| 4,856,524 A | 8/1989 | Baker, Jr. | |
| 4,875,477 A | 10/1989 | Waschke et al. | |
| 4,928,688 A | 5/1990 | Mower | |
| 4,953,551 A | 9/1990 | Mehra et al. | |

(Continued)

FOREIGN PATENT DOCUMENTS

EP 0770407 5/1997

(Continued)

OTHER PUBLICATIONS

Verrier et al., Sleep, dreams, and sudden death: the case for sleep as an autonomic stress test for the heart, 31 Cardiovascular Research 181-211, 1996.

(Continued)

*Primary Examiner* — Charles A Marmor, II
*Assistant Examiner* — Karen E Toth
(74) *Attorney, Agent, or Firm* — Hollingsworth & Funk, LLC

(57) ABSTRACT

An approach for predicting disordered breathing involves detecting one or more conditions associated with disordered breathing. The detected conditions are compared to disordered breathing prediction criteria. A prediction of disordered breathing is performed based on the comparison of the detected conditions to the prediction criteria. At least one of comparing the detected conditions to the prediction criteria and predicting disordered breathing is performed at least in part implantably.

19 Claims, 9 Drawing Sheets

U.S. PATENT DOCUMENTS

| | | |
|---|---|---|
| 4,958,632 A | 9/1990 | Duggan |
| 4,961,423 A | 10/1990 | Canducci |
| 4,972,842 A | 11/1990 | Korten et al. |
| 4,982,738 A | 1/1991 | Griebel |
| 5,010,888 A | 4/1991 | Jadvar et al. |
| 5,024,222 A | 6/1991 | Thacker |
| 5,036,849 A | 8/1991 | Hauck et al. |
| 5,047,930 A | 9/1991 | Martens et al. |
| 5,063,927 A | 11/1991 | Webb et al. |
| 5,105,354 A | 4/1992 | Nishimura |
| 5,123,425 A | 6/1992 | Shannon, Jr. et al. |
| 5,133,353 A | 7/1992 | Hauser |
| 5,146,918 A | 9/1992 | Kallok et al. |
| 5,156,157 A | 10/1992 | Valenta, Jr. et al. |
| 5,170,784 A | 12/1992 | Ramon et al. |
| 5,174,287 A | 12/1992 | Kallok et al. |
| 5,178,156 A | 1/1993 | Takishima et al. |
| 5,179,945 A | 1/1993 | Van Hofwegen et al. |
| 5,183,038 A | 2/1993 | Hoffman et al. |
| 5,187,657 A | 2/1993 | Forbes |
| 5,188,106 A | 2/1993 | Nappholz et al. |
| 5,199,424 A | 4/1993 | Sullivan et al. |
| 5,203,348 A | 4/1993 | Dahl et al. |
| 5,209,229 A | 5/1993 | Gilli |
| 5,211,173 A | 5/1993 | Kallok et al. |
| 5,215,082 A | 6/1993 | Kallok et al. |
| 5,230,337 A | 7/1993 | Dahl et al. |
| 5,233,983 A | 8/1993 | Markowitz |
| 5,245,995 A | 9/1993 | Sullivan et al. |
| 5,259,373 A | 11/1993 | Gruenke et al. |
| 5,261,400 A | 11/1993 | Bardy |
| 5,275,159 A | 1/1994 | Griebel |
| 5,280,791 A | 1/1994 | Lavie |
| 5,284,136 A | 2/1994 | Hauck et al. |
| 5,292,338 A | 3/1994 | Bardy |
| 5,299,118 A | 3/1994 | Martens et al. |
| 5,300,106 A | 4/1994 | Dahl et al. |
| 5,301,677 A | 4/1994 | Hsung |
| 5,313,953 A | 5/1994 | Yomtov et al. |
| 5,314,430 A | 5/1994 | Bardy |
| 5,314,459 A | 5/1994 | Swanson et al. |
| 5,318,597 A | 6/1994 | Hauck et al. |
| 5,330,505 A | 7/1994 | Cohen |
| 5,331,966 A | 7/1994 | Bennett et al. |
| 5,334,222 A | 8/1994 | Salo et al. |
| 5,335,657 A | 8/1994 | Terry, Jr. et al. |
| 5,353,788 A | 10/1994 | Miles |
| 5,360,442 A | 11/1994 | Dahl et al. |
| 5,366,496 A | 11/1994 | Dahl et al. |
| 5,372,606 A | 12/1994 | Lang et al. |
| 5,376,106 A | 12/1994 | Stahmann et al. |
| 5,376,476 A | 12/1994 | Eylon |
| 5,388,578 A | 2/1995 | Yomtov et al. |
| 5,391,200 A | 2/1995 | Kenknight et al. |
| 5,397,342 A | 3/1995 | Heil, Jr. et al. |
| 5,398,682 A | 3/1995 | Lynn |
| 5,411,031 A | 5/1995 | Yomtov |
| 5,411,525 A | 5/1995 | Swanson et al. |
| 5,411,539 A | 5/1995 | Neisz |
| 5,439,482 A | 8/1995 | Adams et al. |
| 5,441,518 A | 8/1995 | Adams et al. |
| 5,466,245 A | 11/1995 | Spinelli et al. |
| 5,468,254 A | 11/1995 | Hahn et al. |
| 5,483,969 A | 1/1996 | Testerman et al. |
| 5,485,851 A | 1/1996 | Erickson |
| 5,511,553 A * | 4/1996 | Segalowitz .................. 600/508 |
| 5,517,983 A | 5/1996 | Deighan et al. |
| 5,520,176 A | 5/1996 | Cohen |
| 5,522,382 A | 6/1996 | Sullivan et al. |
| 5,522,862 A | 6/1996 | Testerman et al. |
| 5,531,779 A | 7/1996 | Dahl et al. |
| 5,540,727 A | 7/1996 | Tockman et al. |
| 5,540,732 A | 7/1996 | Testerman |
| 5,540,734 A | 7/1996 | Zabara |
| 5,545,186 A | 8/1996 | Olson et al. |
| 5,545,202 A | 8/1996 | Dahl et al. |
| 5,549,655 A | 8/1996 | Erickson |
| 5,590,648 A | 1/1997 | Mitchell et al. |
| 5,591,216 A | 1/1997 | Testerman et al. |
| 5,603,732 A | 2/1997 | Dahl et al. |
| 5,605,151 A | 2/1997 | Lynn |
| 5,606,969 A | 3/1997 | Butler et al. |
| 5,620,466 A | 4/1997 | Haefner et al. |
| 5,622,178 A | 4/1997 | Gilham |
| 5,634,938 A | 6/1997 | Swanson et al. |
| 5,641,326 A | 6/1997 | Adams |
| 5,645,570 A | 7/1997 | Corbucci |
| 5,662,688 A | 9/1997 | Haefner et al. |
| 5,693,000 A | 12/1997 | Crosby et al. |
| 5,697,951 A | 12/1997 | Harpstead et al. |
| 5,697,953 A | 12/1997 | Kroll et al. |
| 5,701,894 A | 12/1997 | Cherry et al. |
| 5,704,365 A | 1/1998 | Albrecht et al. |
| 5,713,933 A | 2/1998 | Condie et al. |
| 5,715,812 A | 2/1998 | Deighan et al. |
| 5,724,984 A | 3/1998 | Arnold et al. |
| 5,738,102 A | 4/1998 | Lemelson |
| 5,792,188 A | 8/1998 | Starkweather et al. |
| 5,800,470 A | 9/1998 | Stein et al. |
| 5,802,188 A | 9/1998 | McDonough |
| 5,814,087 A | 9/1998 | Renirie |
| 5,826,579 A | 10/1998 | Remmers et al. |
| 5,827,326 A | 10/1998 | Kroll et al. |
| 5,836,987 A | 11/1998 | Baumann et al. |
| 5,844,680 A | 12/1998 | Sperling |
| 5,855,593 A | 1/1999 | Olson et al. |
| 5,861,011 A | 1/1999 | Stoop |
| 5,876,353 A | 3/1999 | Riff |
| 5,891,023 A | 4/1999 | Lynn |
| 5,895,414 A | 4/1999 | Sanchez-Zambrano |
| 5,902,250 A | 5/1999 | Verrier et al. |
| 5,911,218 A | 6/1999 | DiMarco |
| 5,916,243 A | 6/1999 | KenKnight et al. |
| 5,919,141 A | 7/1999 | Money et al. |
| 5,944,680 A | 8/1999 | Christopherson et al. |
| 5,957,956 A | 9/1999 | Kroll et al. |
| 5,961,446 A | 10/1999 | Beller et al. |
| 5,961,450 A | 10/1999 | Merchant et al. |
| 5,964,778 A | 10/1999 | Fugoso et al. |
| 5,970,975 A | 10/1999 | Estes et al. |
| 5,974,340 A | 10/1999 | Kadhiresan |
| 5,981,011 A | 11/1999 | Overcash et al. |
| 6,015,388 A | 1/2000 | Sackner et al. |
| 6,021,351 A | 2/2000 | Kadhiresan et al. |
| 6,026,320 A | 2/2000 | Carlson et al. |
| 6,044,298 A | 3/2000 | Salo et al. |
| 6,045,513 A | 4/2000 | Stone et al. |
| 6,047,203 A | 4/2000 | Sackner et al. |
| 6,050,940 A | 4/2000 | Braun et al. |
| 6,055,454 A | 4/2000 | Heemels |
| 6,059,725 A | 5/2000 | Steinschneider |
| 6,064,910 A | 5/2000 | Andersson et al. |
| 6,076,015 A | 6/2000 | Hartley et al. |
| 6,091,973 A | 7/2000 | Colla et al. |
| 6,091,986 A | 7/2000 | Keimel |
| 6,099,479 A | 8/2000 | Christopherson et al. |
| 6,105,575 A | 8/2000 | Estes et al. |
| 6,120,441 A | 9/2000 | Griebel |
| 6,126,611 A | 10/2000 | Bourgeois et al. |
| 6,128,534 A | 10/2000 | Park et al. |
| 6,132,384 A | 10/2000 | Christopherson et al. |
| 6,141,581 A | 10/2000 | Olson et al. |
| 6,141,590 A | 10/2000 | Renirie et al. |
| 6,144,866 A | 11/2000 | Miesel et al. |
| 6,148,230 A | 11/2000 | KenKnight |
| 6,155,976 A | 12/2000 | Sackner et al. |
| 6,161,042 A | 12/2000 | Hartley et al. |
| 6,168,568 B1 | 1/2001 | Gavriely |
| 6,181,961 B1 | 1/2001 | Prass |
| 6,190,326 B1 | 2/2001 | McKinnon et al. |
| 6,200,265 B1 | 3/2001 | Walsh et al. |
| 6,212,435 B1 | 4/2001 | Lattner et al. |
| 6,221,011 B1 | 4/2001 | Bardy |
| 6,236,873 B1 | 5/2001 | Holmström |
| 6,240,316 B1 | 5/2001 | Richmond et al. |
| 6,251,126 B1 | 6/2001 | Ottenhoff et al. |
| 6,258,039 B1 | 7/2001 | Okamoto et al. |

| | | |
|---|---|---|
| 6,259,947 B1 | 7/2001 | Olson et al. |
| 6,261,238 B1 | 7/2001 | Gavriely |
| 6,269,269 B1 | 7/2001 | Ottenhoff et al. |
| 6,270,457 B1 | 8/2001 | Bardy |
| 6,272,377 B1 | 8/2001 | Sweeney et al. |
| 6,275,727 B1 | 8/2001 | Hopper et al. |
| 6,277,072 B1 | 8/2001 | Bardy |
| 6,280,380 B1 | 8/2001 | Bardy |
| 6,280,462 B1 | 8/2001 | Hauser et al. |
| 6,285,907 B1 | 9/2001 | Kramer et al. |
| 6,287,264 B1 | 9/2001 | Hoffman |
| 6,303,270 B1 | 10/2001 | Flaim |
| 6,306,088 B1 | 10/2001 | Krausman |
| 6,312,378 B1 | 11/2001 | Bardy |
| 6,331,536 B1 | 12/2001 | Radulovacki et al. |
| 6,336,903 B1 | 1/2002 | Bardy |
| 6,351,669 B1 | 2/2002 | Hartley et al. |
| 6,351,670 B1 | 2/2002 | Kroll |
| 6,353,759 B1 | 3/2002 | Hartley et al. |
| 6,357,444 B1 | 3/2002 | Parker |
| 6,358,203 B2 | 3/2002 | Bardy |
| 6,360,127 B1 | 3/2002 | Ding et al. |
| 6,361,494 B1 | 3/2002 | Lindenthaler |
| 6,361,522 B1 | 3/2002 | Scheiner et al. |
| 6,363,270 B1 | 3/2002 | Colla et al. |
| 6,366,813 B1 | 4/2002 | DiLorenzo |
| 6,368,284 B1 | 4/2002 | Bardy |
| 6,368,287 B1 | 4/2002 | Hadas |
| 6,371,922 B1 | 4/2002 | Baumann et al. |
| 6,375,614 B1 | 4/2002 | Braun et al. |
| 6,375,621 B1 | 4/2002 | Sullivan |
| 6,375,623 B1 | 4/2002 | Gavriely |
| 6,397,845 B1 | 6/2002 | Burton |
| 6,398,728 B1 | 6/2002 | Bardy |
| 6,398,739 B1 | 6/2002 | Sullivan et al. |
| 6,409,675 B1 | 6/2002 | Turcott |
| 6,409,676 B2 | 6/2002 | Ruton et al. |
| 6,411,848 B2 | 6/2002 | Kramer et al. |
| 6,415,174 B1 | 7/2002 | Bebehani et al. |
| 6,415,183 B1 | 7/2002 | Scheiner et al. |
| 6,424,865 B1 | 7/2002 | Ding |
| 6,430,439 B1 | 8/2002 | Wentkowski et al. |
| 6,431,171 B1 | 8/2002 | Burton |
| 6,438,407 B1 | 8/2002 | Ousdigian et al. |
| 6,438,410 B2 | 8/2002 | Hsu et al. |
| 6,440,066 B1 | 8/2002 | Bardy |
| 6,442,413 B1 | 8/2002 | Silver |
| 6,449,503 B1 | 9/2002 | Hsu |
| 6,450,957 B1 | 9/2002 | Yoshimi |
| 6,454,708 B1 | 9/2002 | Ferguson et al. |
| 6,459,929 B1 | 10/2002 | Hopper et al. |
| 6,463,326 B1 | 10/2002 | Hartley et al. |
| 6,468,219 B1 | 10/2002 | Njemanze |
| 6,480,733 B1 | 11/2002 | Turcott |
| 6,487,443 B2 | 11/2002 | Olson et al. |
| 6,491,639 B1 | 12/2002 | Turcott |
| 6,497,658 B2 | 12/2002 | Roizen et al. |
| 6,512,940 B1 | 1/2003 | Brabec et al. |
| 6,522,915 B1 | 2/2003 | Ceballos et al. |
| 6,542,775 B2 | 4/2003 | Ding et al. |
| 6,564,106 B2 | 5/2003 | Guck et al. |
| 6,572,543 B1 | 6/2003 | Christopherson et al. |
| 6,574,507 B1 | 6/2003 | Bonnet |
| 6,580,944 B1 | 6/2003 | Katz et al. |
| 6,589,188 B1 | 7/2003 | Street et al. |
| 6,595,927 B2 | 7/2003 | Pitts-Crick et al. |
| 6,597,951 B2 | 7/2003 | Kadhiresan et al. |
| 6,600,949 B1 * | 7/2003 | Turcott .................. 600/518 |
| 6,606,993 B1 | 8/2003 | Wiesmann et al. |
| 6,607,509 B2 | 8/2003 | Bobroff et al. |
| 6,615,083 B2 | 9/2003 | Kupper |
| 6,622,046 B2 | 9/2003 | Fraley et al. |
| 6,628,986 B1 | 9/2003 | Mouchawar et al. |
| 6,641,542 B2 | 11/2003 | Cho et al. |
| 6,694,186 B2 | 2/2004 | Bardy |
| 6,704,590 B2 | 3/2004 | Haldeman |
| 6,708,058 B2 | 3/2004 | Kim et al. |
| 6,723,055 B2 | 4/2004 | Hoffman |
| 6,731,984 B2 | 5/2004 | Cho et al. |
| 6,741,885 B1 | 5/2004 | Park et al. |
| 6,752,765 B1 | 6/2004 | Jensen et al. |
| 6,752,766 B2 | 6/2004 | Kowallik et al. |
| 6,754,528 B2 | 6/2004 | Bardy et al. |
| 6,765,062 B2 | 7/2004 | Chin et al. |
| 6,770,022 B2 | 8/2004 | Mechlenburg et al. |
| 6,773,404 B2 | 8/2004 | Poezevera et al. |
| 6,778,860 B2 | 8/2004 | Ostroff et al. |
| 6,786,866 B2 | 9/2004 | Odagiri et al. |
| 6,788,974 B2 | 9/2004 | Bardy et al. |
| 6,810,287 B2 | 10/2004 | Zhu et al. |
| 6,830,548 B2 | 12/2004 | Bonnet |
| 6,834,204 B2 | 12/2004 | Ostroff et al. |
| 6,850,801 B2 | 2/2005 | Kieval et al. |
| 6,856,835 B2 | 2/2005 | Bardy et al. |
| 6,865,417 B2 | 3/2005 | Rissmann et al. |
| 6,866,044 B2 | 3/2005 | Bardy et al. |
| 6,881,192 B1 | 4/2005 | Park |
| 6,890,306 B2 | 5/2005 | Poezevera |
| 6,892,095 B2 | 5/2005 | Salo |
| 6,904,320 B2 | 6/2005 | Park et al. |
| 6,912,419 B2 | 6/2005 | Hill et al. |
| 6,927,721 B2 | 8/2005 | Ostroff |
| 6,928,324 B2 | 8/2005 | Park et al. |
| 6,937,907 B2 | 8/2005 | Bardy et al. |
| 6,950,705 B2 | 9/2005 | Bardy et al. |
| 6,952,608 B2 | 10/2005 | Ostroff |
| 6,952,610 B2 | 10/2005 | Ostroff et al. |
| 6,954,670 B2 | 10/2005 | Ostroff |
| 6,959,214 B2 | 10/2005 | Pape et al. |
| 6,961,619 B2 | 11/2005 | Casey |
| 6,964,641 B2 | 11/2005 | Cho et al. |
| 6,988,003 B2 | 1/2006 | Bardy et al. |
| 6,988,498 B2 | 1/2006 | Berthon-Jones et al. |
| 6,993,389 B2 | 1/2006 | Ding et al. |
| 6,999,817 B2 | 2/2006 | Park et al. |
| 7,025,729 B2 | 4/2006 | de Chazal et al. |
| 7,025,730 B2 | 4/2006 | Cho et al. |
| 7,027,861 B2 | 4/2006 | Thompson |
| 7,027,871 B2 | 4/2006 | Burnes et al. |
| 7,039,459 B2 | 5/2006 | Bardy et al. |
| 7,039,465 B2 | 5/2006 | Bardy et al. |
| 7,043,299 B2 | 5/2006 | Erlinger et al. |
| 7,050,851 B2 | 5/2006 | Plombon et al. |
| 7,065,407 B2 | 6/2006 | Bardy et al. |
| 7,065,409 B2 | 6/2006 | Mazar |
| 7,065,410 B2 | 6/2006 | Bardy et al. |
| 7,069,080 B2 | 6/2006 | Bardy et al. |
| 7,076,296 B2 | 7/2006 | Rissmann et al. |
| 7,081,095 B2 | 7/2006 | Lynn et al. |
| 7,090,682 B2 | 8/2006 | Sanders et al. |
| 7,092,754 B2 | 8/2006 | Bardy et al. |
| 7,092,755 B2 | 8/2006 | Florio |
| 7,117,036 B2 | 10/2006 | Florio |
| 7,120,495 B2 | 10/2006 | Bardy et al. |
| 7,127,290 B2 | 10/2006 | Girouard et al. |
| 7,127,300 B2 | 10/2006 | Mazar et al. |
| 7,130,687 B2 | 10/2006 | Cho et al. |
| 7,146,212 B2 | 12/2006 | Bardy et al. |
| 7,149,574 B2 | 12/2006 | Yun et al. |
| 7,149,575 B2 | 12/2006 | Ostroff et al. |
| 7,155,278 B2 | 12/2006 | King et al. |
| 7,189,204 B2 | 3/2007 | Ni et al. |
| 7,194,302 B2 | 3/2007 | Bardy et al. |
| 7,194,309 B2 | 3/2007 | Ostroff et al. |
| 7,194,313 B2 | 3/2007 | Libbus |
| 7,206,635 B2 | 4/2007 | Cho et al. |
| 7,207,945 B2 | 4/2007 | Bardy |
| 7,212,862 B2 | 5/2007 | Park et al |
| 7,225,013 B2 | 5/2007 | Geva et al. |
| 7,252,640 B2 | 8/2007 | Ni et al. |
| 7,308,311 B2 | 12/2007 | Sorensen et al. |
| 7,396,333 B2 | 7/2008 | Stahmann et al. |
| 7,400,928 B2 | 7/2008 | Hatlestsad |
| 7,428,468 B2 | 9/2008 | Takemura et al. |
| 7,438,686 B2 | 10/2008 | Cho et al. |
| 7,469,697 B2 | 12/2008 | Lee et al. |
| 7,515,969 B2 | 4/2009 | Tockman et al. |
| 7,704,211 B1 * | 4/2010 | Koh .................. 600/486 |

| | | | |
|---|---|---|---|
| 2002/0035377 A1 | 3/2002 | Bardy et al. | |
| 2002/0035378 A1 | 3/2002 | Bardy et al. | |
| 2002/0035379 A1 | 3/2002 | Bardy et al. | |
| 2002/0035381 A1 | 3/2002 | Bardy et al. | |
| 2002/0082658 A1 | 6/2002 | Heinrich et al. | |
| 2002/0095184 A1 | 7/2002 | Bardy et al. | |
| 2002/0107544 A1 | 8/2002 | Ostroff et al. | |
| 2002/0107545 A1 | 8/2002 | Rissmann et al. | |
| 2003/0023175 A1 | 1/2003 | Arzbaecher et al. | |
| 2003/0088027 A1 | 5/2003 | Chin et al. | |
| 2003/0153953 A1* | 8/2003 | Park et al. | 607/17 |
| 2003/0178031 A1 | 9/2003 | Du Pen et al. | |
| 2003/0195571 A1 | 10/2003 | Burnes et al. | |
| 2003/0199945 A1 | 10/2003 | Ciulla | |
| 2003/0204213 A1 | 10/2003 | Jensen et al. | |
| 2003/0212436 A1 | 11/2003 | Brown | |
| 2003/0216789 A1 | 11/2003 | Deem et al. | |
| 2004/0059240 A1 | 3/2004 | Cho et al. | |
| 2004/0127799 A1* | 7/2004 | Sorensen et al. | 600/481 |
| 2004/0128161 A1* | 7/2004 | Mazar et al. | 705/2 |
| 2004/0133079 A1* | 7/2004 | Mazar et al. | 600/300 |
| 2004/0172080 A1* | 9/2004 | Stadler et al. | 607/17 |
| 2004/0215240 A1 | 10/2004 | Lovett et al. | |
| 2004/0230229 A1 | 11/2004 | Lovett et al. | |
| 2004/0230230 A1 | 11/2004 | Lindstrom | |
| 2005/0004615 A1 | 1/2005 | Sanders | |
| 2005/0039745 A1 | 2/2005 | Stahmann et al. | |
| 2005/0042589 A1 | 2/2005 | Hatlestad et al. | |
| 2005/0043652 A1 | 2/2005 | Lovett et al. | |
| 2005/0043772 A1 | 2/2005 | Stahmann et al. | |
| 2005/0065567 A1 | 3/2005 | Lee et al. | |
| 2005/0085865 A1 | 4/2005 | Tehrani | |
| 2005/0145246 A1 | 7/2005 | Hartley et al. | |
| 2005/0288728 A1 | 12/2005 | Libbus et al. | |
| 2007/0161873 A1 | 7/2007 | Ni et al. | |
| 2007/0282215 A1 | 12/2007 | Ni et al. | |
| 2008/0045852 A1* | 2/2008 | Hatlestsad et al. | 600/534 |

FOREIGN PATENT DOCUMENTS

| | | |
|---|---|---|
| EP | 0940155 | 9/1999 |
| EP | 1151718 | 11/2001 |
| EP | 1162125 | 12/2001 |
| EP | 1172125 | 1/2002 |
| EP | 1317943 | 6/2003 |
| EP | 0750920 | 12/2003 |
| WO | WO8402080 | 7/1984 |
| WO | WO9203983 | 3/1992 |
| WO | WO9220402 | 11/1992 |
| WO | WO9904841 | 4/1999 |
| WO | WO0001438 | 1/2000 |
| WO | WO0017615 | 3/2000 |
| WO | WO0240096 | 5/2002 |
| WO | WO02087696 | 11/2002 |
| WO | WO03063954 | 8/2003 |

OTHER PUBLICATIONS

Verrier et al., Sleep Related Cardiovascular Risk: New Home-Based Monitoring Technology for Improved Diagnosis and Therapy, 2 A.N.E. 158-175, 1997.
Waldemark, Katrina et al., Detection of Apnea Using Short Window FFT Technique and Artificial Neural Network, SPIE, International Society for Optical Engineering, vol. 3390, pp. 122-133, 1998.
Weber et al., Effects of CPAP and BIPAP on stroke volume in patients with obstructive sleep apnea syndrome. Pneumolgie Mar. 1995; 49(3):233-5. Translated Abstract only.
Aircraft Noise and Sleep Disturbance: Final Report, prepared by the Civil Aviation Authority London on behalf of the Department of Trade, Aug. 1980 (CAA Report).
Ajilore et al., Nightcap: Laboratory and home-based evaluation of a portable sleep monitor, 32 Psychophysiology, 32-98, 1995. Abstract only.
Bilgutay et al., A new concept in the treatment of hypertension utilizing an implantable electronic device: Baropacer. Trans. Am. Society Artificial Internal Organs. 1964. vol. 10, pp. 387-395.
Bradley et al., Cardiac Output Response to Continuous Positive Airway Pressure in Congestive Heart Failure, 145 Am. Rev. Respir. Dis. 377-382 1992.
Bradley et al., Pathophysiologic and Therapeutic Implications of Sleep Apnea in Congestive Heart Failure, Toronto, Ontario, Canada, Journal of Cardiac Failure, vol. 2, No. 3, pp. 223-240.
Bradley et al., Sleep Apnea and Heart Failure, Park I: Obstructive Sleep Apnea, 107 Circulation 1671-1678, 2003.
Buda et al., Effect of Intrathoracic Pressure on Left Ventricular Performance, 301 Engl. J. Med. 453-459, 1979. Abstract only.
Calvin et al., Positive End-Expiratory Pressure (PEEP) Does Not Depress Left Ventricular Function in Patients With Pulmonary Edema, 124 Am. Rev. Respir. Dis. 121-128, 1981. Abstract only.
Coleridge et al., The distribution, connexions and histology of baroreceptors in the pulmonary artery, with some observations on the sensory innervation of the ductus arteriosus. Physiology. May 1961. vol. 156, pp. 591-602.
De Hoyos et al., Haemodynamic Effects of Continuous Positive Airway Pressure in Humans With Normal and Impaired Left Ventricular Function, 88 Clin. Sci. (Lond). 173-8, 1995. Abstract only.
Garrigue et al., Benefit of Atrial Pacing in Sleep Apnea Syndrome, N. Engl. J. Med., vol. 346, No. 6, pp. 404-412, Feb. 7, 2002.
Giardino et al., Respiratory Sinus Arrhythmia is Associated with the Efficiency of Pulmonary Gas Exchange in Healthy Humans, 284 Am. J. Physiol. H1585-1591, 2003. Abstract only.
Gradaus et al., Nonthoracotomy Implantable Cardioverter Defibrillator Placement in Children: Use of a Subcutaneous Array Leads and Abdominally Placed Implantable Cardioverter Defibrillators in Children, J. of Cardiovascular Electrophysiology, vol. 12, No. 3, pp. 356-360, Mar. 2001.
Hanson et al., Cardiac Gated Ventilation, 2433 SPIE 303-308, 1995.
Hartz et al., New Approach to Defibrillator Insertion, J. Thoracic Cardiovascular Surgery, vol. 97, pp. 920-922, 1989.
Hilton et al., Evaluation of Frequency and Time-frequency Spectral Analysis of Heart Rate Variability as a Diagnostic Marker of the Sleep Apnea Syndrome. Med Biol Eng Comput Nov. 1999, 37(6), 760-9. Abstract only.
Kaye et al., Acute Effects of Continuous Positive Airway Pressure on Cardiac Sympathetic Tone in Congestive Heart Failure, 103 Circulation 2336-24338, 2001.
Kolettis et al., Submammary Implantation of a Cardioverter-Defibrillator with a Nonthoractomy Lead System, Am. Heart J., vol. 126, pp. 1222-1223, Nov. 1993.
Laude et al., Effects of Breathing Pattern on Blood Pressure and Heart Rate Oscillations in Humans, 20 Clin. Exp. Pharmol. Phisiol 619, 625, 1993. Abstract only.
Leng et al., Lead Configuration for Defibrillator Implantation in a Patient with Congenital Heart Disease and a Mechanical Prosthetic Tricuspid Valve, PACE, vol. 24, No. 8, pp. 1291-1292, Aug. 2001.
Lenique et al., Ventilatory and Hemodynamic Effects of Continuous Positive Airway Pressure in Left Heart Failure, 155 Am. J. Respir. Crit. Care Med. 500-505, 1997. Abstract only.
Lugaresi et al., Snoring, 39 Electroencephalogr. Clin. Neurophysiol. 59-64, 1975.
Mansfield et al., Effects of Continuous Positive Airway Pressure on Lung Function in Patients with Chronic Obstructive Pulmonary Disease and Sleep Disordered Breathing, Respirology 365-70, 1999. Abstract only.
Mehta et al., Effects of Continuous Positive Airway Pressure on Cardiac Volumes In Patients With Ischemic and Dilated Cardiomyopathy, 161 Am. J. Respir. Crit. Care Med. 128-134, 2000.
Naughton et al., Effects of Continuous Positive Airway Pressure on Intrathoracic and Left Ventricular Transmural Pressure in Congestive Heart Failure, 91 Circulation 1725-1731, 1995, pp. 1-25.
Neil et al., Effects of electrical stimulation of the aortic nerve on blood pressure and respiration in cats and rabbits under chloralose and nembutal anaesthesia. Journal of Physiology. Sep. 1949. vol. 109 (3-4), pp. 392-401.
Park et al., Use of an Implantable Cardioverter Defibrillator in an Eight-Month-Old Infant with Ventricular Fibrillation Arising from a Myocardial Fibroma, PACE, vol. 22, No. 1, pp. 138-139, Jan. 1999.
Peters et al. Tempral and spatial summation caused by aortic nerve stimulation in rabbits. Effects of stimulation frequencies and amplitudes. Journal of the Autonomic Nervous System. 1989 vol. 27, pp. 193-205, Abstract only.

Pinsky et al., Hemodynamic Effect of Cardiac Cycle-Specific Increases in Intrathoracic Pressure, 6 J. Appl. Physiol. 604-612, 1986. Abstract only.

Potkin et al., Effect of positive end-expiratory pressure on right and left ventricular function in patients with the adult respiratory distress syndrome, 135 Am. Rev. Respir. Dis. 307-311, 1987. Abstract only.

Reddel et al., Analysis of Adherence to Peak Flow Monitoring When Recording of Data is Electronic, BMJ 146-147, 2002.

Roche et al., Screening of Obstructive Sleep Apnea Syndrome by Heart Rate Variability Analysis. Circulation Sep. 28, 1999; 100(13):1411-5.

Sato et al., Novel Therapeutic Strategy against Central Baroreflex Failure: A Bionic Baroreflex System. Circulation. Jul. 1999 vol. 100, pp. 299-304.

Satoh et al., Role of Hypoxic Drive in Regulation of Postapneic Ventilation During Sleep in Patients with Obstructive Sleep Apnea, Am Rev Respir Dis, Mar. 1991 143 (3): 481-485. Abstract only.

Scharf, Effects of Continuous Positive Airway Pressure on Cardiac Output in Experimental Heart Failure, 19 Sleep S240-2 1996. Abstract only.

Schuder et al., Experimental Ventricular Defibrillation with an Automatic and Completely Implanted System, Trans. Am. Soc. Artif. Int. Organs, vol. 16, pp. 207-212, 1970.

Schuder et al., Transthoracic Ventricular Defibrillation in the Dog with Truncated and Untruncated Exponential Stimuli, IEEE Trans. On Bio-Medical Engin., vol. BME-18, No. 6, pp. 410-415, Nov. 1971.

Schuder et al., Ventricular Defibrillation in the Dog Using Implanted and Partially Implanted Electrode Systems, Am. J. Of Cardiology, vol. 33, pp. 243-247, Feb. 1974.

Smits et al., Defibrillation Threshold (DFT) Model of a Fully Subcutaneous ICD System, Europace Supplements, vol. 2, Jun. 2001 at col. 778, p. B83.

Steltner et al., Diagnosis of Sleep Apnea by Automatic Analysis of Nasal Pressure and Forced Oscillation Impedance. Am. Journal Respiratory Critical Care Medicine, vol. 165, pp. 940-944, 2002.

Stirbis et al., Optmizing the Shape of Implanted Artificial Pacemakers, Kaunas Medical Institute. Translated from Meditsinskaya Tekhnika, No. 6, pp. 25-27, 1986.

Thrasher et al. Unloading arterial baroreceptors causes neurogenic hypertension. American Journal Physiol. Regulatory Integrative Comp. Physiol. 2002. vol. 282, R1044-R1053.

Vanninen et al., Cardiac Sympathovagal Balance During Sleep Apnea Episodes. Clin Physiol May 1996; 16(3):209-16.

Office Action from U.S. Appl. No. 10/643,016 dated Jun. 29, 2007, 18 pages.

International Preliminary Report on Patentability dated Mar. 2, 2006 from PCT Application No. PCT/US2004/026883, 9 pages.

International Search Report and Written Opinion dated Jun. 12, 2004 from PCT Application No. PCT/US2004/026883, 15 pages.

Office Action dated May 25, 2010 from Japanese Application No. 2006-524027, 4 pages.

Office Action dated Jul. 14, 2006 from European Application No. 04781543.6, 3 pages.

Office Action Response dated Nov. 16, 2006 from European Application No. 04781543.6, 6 pages.

Office Action dated Feb. 8, 2007 from European Application No. 04781543.6, 3 pages.

Office Action Response dated Aug. 6, 2007 from European Application No. 04781543.6, 12 pages.

Office Action dated Dec. 21, 2007 from European Application No. 04781543.6, 6 pages.

Notice of Allowance dated Dec. 14, 2007 from U.S. Appl. No. 10/643,016, 8 pages.

Office Action Response dated Oct. 1, 2007 from U.S. Appl. No. 10/643,016, 16 pages.

Office Action Response dated May 11, 2007 from U.S. Appl. No. 10/643,016, 20 pages.

Office Action dated Apr. 18, 2007 from U.S. Appl. No. 10/643,016, 7 pages.

Office Action Response dated Jan. 22, 2007 from U.S. Appl. No. 10/643,016, 17 pages.

Office Action dated Nov. 14, 2006 from U.S. Appl. No. 10/643,016, 7 pages.

Office Action Response dated Nov. 17, 2010 from U.S. Appl. No. 12/724,723, 7 pages.

Office Action dated Feb. 4, 2011 from U.S. Appl. No. 12/724,723, 7 pages.

* cited by examiner ly to prediction of disordered breathing using an implantable device.
PREDICTION OF DISORDERED BREATHING

RELATED APPLICATIONS

This application is a continuation of U.S. patent application Ser. No. 10/643,016, filed on Aug. 18, 2003, now U.S. Pat. No. 7,396,333 which is hereby incorporated herein by reference.

FIELD OF THE INVENTION

The present invention relates generally to prediction of disordered breathing using an implantable device.

BACKGROUND OF THE INVENTION

Disordered breathing is associated with a wide spectrum of respiratory conditions that involve disruption of the normal respiratory cycle. Although disordered breathing typically occurs during sleep, the condition may also occur while the patient is awake. Respiratory disruption can be particularly serious for patients concurrently suffering from cardiovascular deficiencies, such as congestive heart failure. Unfortunately, disordered breathing is often undiagnosed. If left untreated, the effects of disordered breathing may result in serious health consequences for the patient.

Various types of disordered respiration have been identified, including apnea, hypopnea, tachypnea, and periodic breathing. Apnea is a fairly common disorder characterized by periods of interrupted breathing. Apnea is typically classified based on its etiology. One type of apnea, denoted obstructive apnea, occurs when the patient's airway is obstructed by the collapse of soft tissue in the rear of the throat. Central apnea is caused by a derangement of the central nervous system control of respiration. The patient ceases to breathe when control signals from the brain to the respiratory muscles are absent or interrupted. Mixed apnea is a combination of the central and obstructive apnea types. Regardless of the type of apnea, people experiencing an apnea event stop breathing for a period of time. The cessation of breathing may occur repeatedly during sleep, sometimes hundreds of times a night and sometimes for a minute or longer.

In addition to apnea, other types of disordered respiration have been identified, including hypopnea (shallow breathing), tachypnea (rapid breathing), hyperpnea (heavy breathing), and dyspnea (labored breathing). Combinations of the respiratory cycles described above may be observed, including, for example, periodic breathing and Cheyne-Stokes respiration (CSR). Periodic breathing is characterized by cyclic respiratory patterns that may exhibit rhythmic rises and falls in tidal volume. Cheyne-Stokes respiration is a specific form of periodic breathing wherein the tidal volume decreases to zero resulting in apneic intervals. The breathing interruptions of periodic breathing and CSR are predominately central in nature but may occasionally be obstructive in nature. Cheyne-Stokes respiration is frequently observed in patients with congestive heart failure (CHF) and is associated with an increased risk of accelerated CHF progression.

Although disordered breathing is more common during sleep, disordered breathing may also occur while the patient is awake. When disordered breathing occurs during sleep, the patient may briefly arouse in order to resume breathing. The frequent interruptions during sleep result in extremely fragmented sleep of poor quality. An adequate duration and quality of sleep is required to maintain physiological homeostasis. Untreated, disordered breathing may have a number of adverse health and quality of life consequences ranging from high blood pressure and other cardiovascular diseases to cognitive impairment, headaches, impaired driving skills resulting in increased vehicular accidents, and degradation of social and work related activities.

SUMMARY OF THE INVENTION

Various embodiments of present invention involve methods, devices, and systems for predicting disordered breathing.

An embodiment of the invention involves an automated method of predicting disordered breathing in a patient. One or more conditions associated with disordered breathing are detected and compared to one or more sets of disordered breathing prediction criteria. Disordered breathing is predicted based on the comparison. At least one of comparing the conditions to the disordered breathing prediction criteria and predicting the disordered breathing is performed at least in part implantably.

In another embodiment of the invention, a method for predicting disordered breathing involves detecting one or more conditions predisposing a patient to disordered breathing. The predisposing conditions are compared to one or more sets of disordered breathing prediction criteria. Disordered breathing is predicted based on the comparison. At least one of comparing the predisposing conditions to the one or more sets of disordered breathing prediction criteria and predicting the disordered breathing is performed at least in part implantably.

Yet another embodiment of the invention involves detecting one or more precursor conditions associated with disordered breathing. The precursor conditions are compared to one or more sets of disordered breathing prediction criteria. Disordered breathing is predicted based on the comparison. At least one of comparing the precursor conditions to the one or more sets of disordered breathing prediction criteria and predicting the disordered breathing is performed at least in part implantably.

In a further embodiment of the invention, a medical device includes a detector system and a prediction engine. The detector system is configured to detect one or more conditions associated with disordered breathing. The prediction engine is coupled to the detector system and is configured to compare the one or more detected conditions to one or more sets of disordered breathing prediction criteria and to predict disordered breathing based on the comparison. The prediction engine includes at least one implantable component.

Another embodiment of the invention involves an automated disordered breathing prediction system. The system includes means for detecting one or more conditions associated with disordered breathing, means for comparing the detected one or more conditions to one or more sets of disordered breathing prediction criteria and means for predicting disordered breathing based on the comparison. At least one of the means for comparing and the means for predicting includes an implantable component.

In yet another embodiment of the invention, an automated system for predicting disordered breathing includes means for detecting conditions predisposing the patient to disordered breathing. The system further includes means for comparing the predisposing conditions to one or more sets of disordered breathing prediction criteria and means for predicting disordered breathing based on the comparison. At least one of the means for comparing the predisposing conditions to the one or more sets of prediction criteria, and the means for predicting disordered breathing includes an implantable component.

In yet a further embodiment of the invention, an automated system for predicting disordered breathing includes means for detecting precursor conditions associated with disordered breathing. The system further includes means for comparing the precursor conditions to one or more sets of disordered breathing prediction criteria and means for predicting disordered breathing based on the comparison. At least one of the means for comparing the precursor conditions to the one or more sets of disordered breathing prediction criteria and means for predicting disordered breathing includes an implantable component.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1:
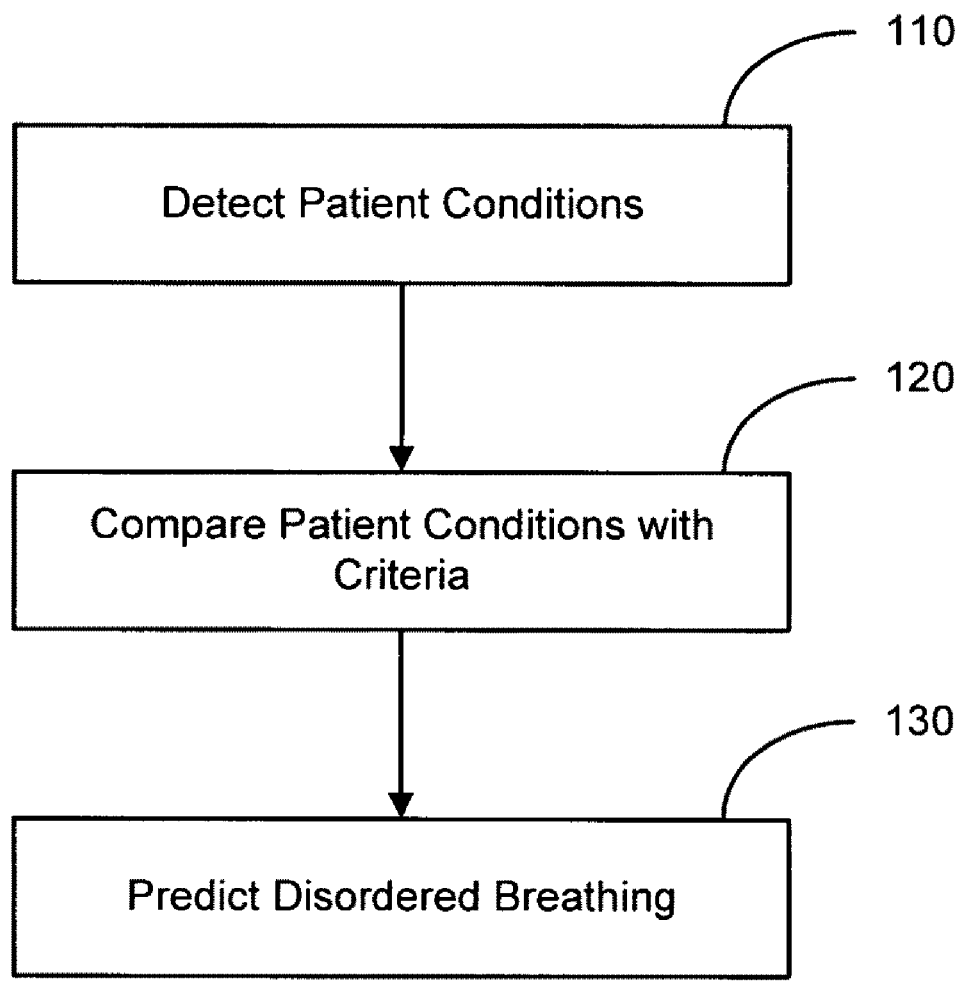
FIG. 1 is a flow graph of a method for predicting disordered breathing in accordance with embodiments of the invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings which form a part hereof, and in which are shown, by way of illustration, various embodiments by which the invention may be practiced. It is to be understood that other embodiments may be utilized. Structural and functional changes may be made without departing from the scope of the present invention.

A significant percentage of patients between the ages of 30 and 60 years experience some symptoms of disordered breathing. Sleep disordered breathing is associated with excessive daytime sleepiness, systemic hypertension, increased risk of stroke, angina, and myocardial infarction. Disordered breathing is particularly prevalent among congestive heart failure patients, and may contribute to the progression of heart failure.

Disordered breathing occurs most often when the patient is asleep and may result in highly fragmented sleep. Methods for collecting data and evaluating sleep quality are described in commonly owned U.S. patent application entitled "Sleep Quality Data Collection and Evaluation," identified under Ser. No. 10/642,998, concurrently filed with this patent application and incorporated by reference in its entirety.

Various therapies have been developed to treat central or obstructive disordered breathing episodes. Obstructive apnea has been associated with prolapse of the tongue and its surrounding structure into the pharynx, thus occluding the respiratory pathway. A commonly prescribed treatment for obstructive apnea is continuous positive airway pressure (CPAP). A CPAP device delivers air pressure through a nasal mask worn by the patient. The application of continuous positive airway pressure keeps the patient's throat open, reducing or eliminating the obstruction causing apnea.

Another therapy directed to treating obstructive apnea involves nerve stimulation. Prolapse of the tongue muscles has been attributed to diminishing neuromuscular activity of the upper airway. A treatment for obstructive sleep apnea involves compensating for the decreased muscle activity by electrical activation of the tongue muscles. The hypoglossal nerve innervates the protrusor and retractor tongue muscles. An appropriately applied electrical stimulation to the hypoglossal nerve may prevent backward movement of the tongue, thus preventing the tongue from obstructing the airway.

Cardiac stimulation may be used as a therapy for disordered breathing. A therapy method using cardiac pacing is described in commonly owned U.S. Pat. No. 7,720,541, incorporated herein by reference in its entirety. The cardiac stimulation methods described use adaptive therapy to reduce an impact of the therapy on the patient.

The present invention involves a method and system for predicting disordered breathing. Such a prediction may be used for example, for diagnostic purposes, to alert the patient that disordered breathing is likely to occur. Alternatively or additionally, the prediction may facilitate therapy by allowing the patient to take preventative steps, for example, by beginning a predetermined therapy regimen. Further, the prediction of disordered breathing may also be used to automatically initiate disordered breathing therapy to prevent or mitigate the predicted disordered breathing.

The flowchart of FIG. 1 illustrates a method for predicting disordered breathing according to various embodiments of the invention. The method involves detecting 110 conditions associated with disordered breathing and comparing 120 the detected conditions to one or more sets of disordered breathing prediction criteria. The detected conditions may include, for example, one or more of the representative set of conditions listed in Table 1 below. If the detected conditions are consistent with a set of prediction criteria, disordered breathing is predicted 130. Optionally, a set of verification criteria may be checked prior to the final prediction determination to enhance prediction accuracy.

Conditions associated with disordered breathing used in connection with disordered breathing detection may include both physiological and contextual (e.g. non-physiological) conditions. The physiological conditions may include a broad category of conditions associated with the internal physiological conditions of the patient. Physiological conditions may be further subdivided, for example, into conditions of the cardiovascular, respiratory, and nervous systems, blood chemistry, body-related, e.g., posture and activity, in addition to respiration and/or sleep quality, and comfort during therapy as reported by the patient.

Contextual conditions generally encompass patient-external or background conditions. Contextual conditions may be broadly defined to include, for example, present environmental conditions such as patient location, ambient temperature, humidity, air pollution index, as well as historical/background conditions relating to the patient, including the patient's normal sleep time and the patient's medical history, for example. Methods and systems for detecting some contextual conditions, including, for example, proximity to bed detection, are described in commonly owned U.S. Pat. No. 7,400,928, which is incorporated by reference herein in its entirety.

Table 1 provides a representative set of conditions that may be used in connection with predicting disordered breathing. Table 1 also provides examples of sensing methods that may be employed to sense the conditions.

TABLE 1

| Condition Type | | Condition | Sensor type or Detection method |
|---|---|---|---|
| Physiological | Cardiovascular System | Heart rate | EGM, ECG |
| | | Heart rate variability | |
| | | QT interval | |
| | | Ventricular filling pressure | Intracardiac pressure sensor |
| | | Blood pressure | Blood pressure sensor |
| | Respiratory System | Snoring | Accelerometer |
| | | | Microphone |
| | | Respiration pattern (Tidal volume Minute ventilation Respiratory rate) | Transthoracic impedance sensor (AC) |
| | | Patency of upper airway | Intrathoracic impedance sensor |
| | | Pulmonary congestion | Transthoracic impedance sensor (DC) |
| | Nervous System | Sympathetic nerve activity | Muscle sympathetic nerve Activity sensor |
| | | Brain activity | EEG |
| | Blood Chemistry | CO2 saturation | Blood analysis |
| | | O2 saturation | |
| | | Blood alcohol content | |
| | | Adrenalin | |
| | | B-type Natriutetic Peptide (BNP) | |
| | | C-Reactive Protein | |
| | | Drug/Medication/Tobacco use | |
| | Muscle System | Muscle atonia | EMG |
| | | Eye movement | EOG |
| | | Patient activity | Accelerometer, MV, etc. |
| | | Limb movements | Accelerometer, EMG |
| | | Jaw movements | |
| Contextual (non-physiological) | Environmental | Ambient temperature | Thermometer |
| | | Humidity | Hygrometer |
| | | Pollution | Air quality website |
| | | Time | Clock |
| | | Barometric pressure | Barometer |
| | | Ambient noise | Microphone |
| | | Ambient light | Photodetector |
| | Body-related | Posture | Posture sensor |
| | | Altitude | Altimeter |
| | | Location | GPS, proximity sensor |
| | | Proximity to bed | Proximity to bed sensor |
| | Historical/Background | Historical sleep time | Patient input, previously detected sleep onset times |
| | | Medical history | Patient input device |
| | | Age | |
| | | Recent exercise | |
| | | Weight | |
| | | Gender | |
| | | Body mass index | |
| | | Neck size | |
| | | Emotional state | |
| | | Psychological history | |
| | | Daytime sleepiness | |
| | | Patient perception of sleep quality | |
| | | Drug, alcohol, nicotine use | |

Figure 2:
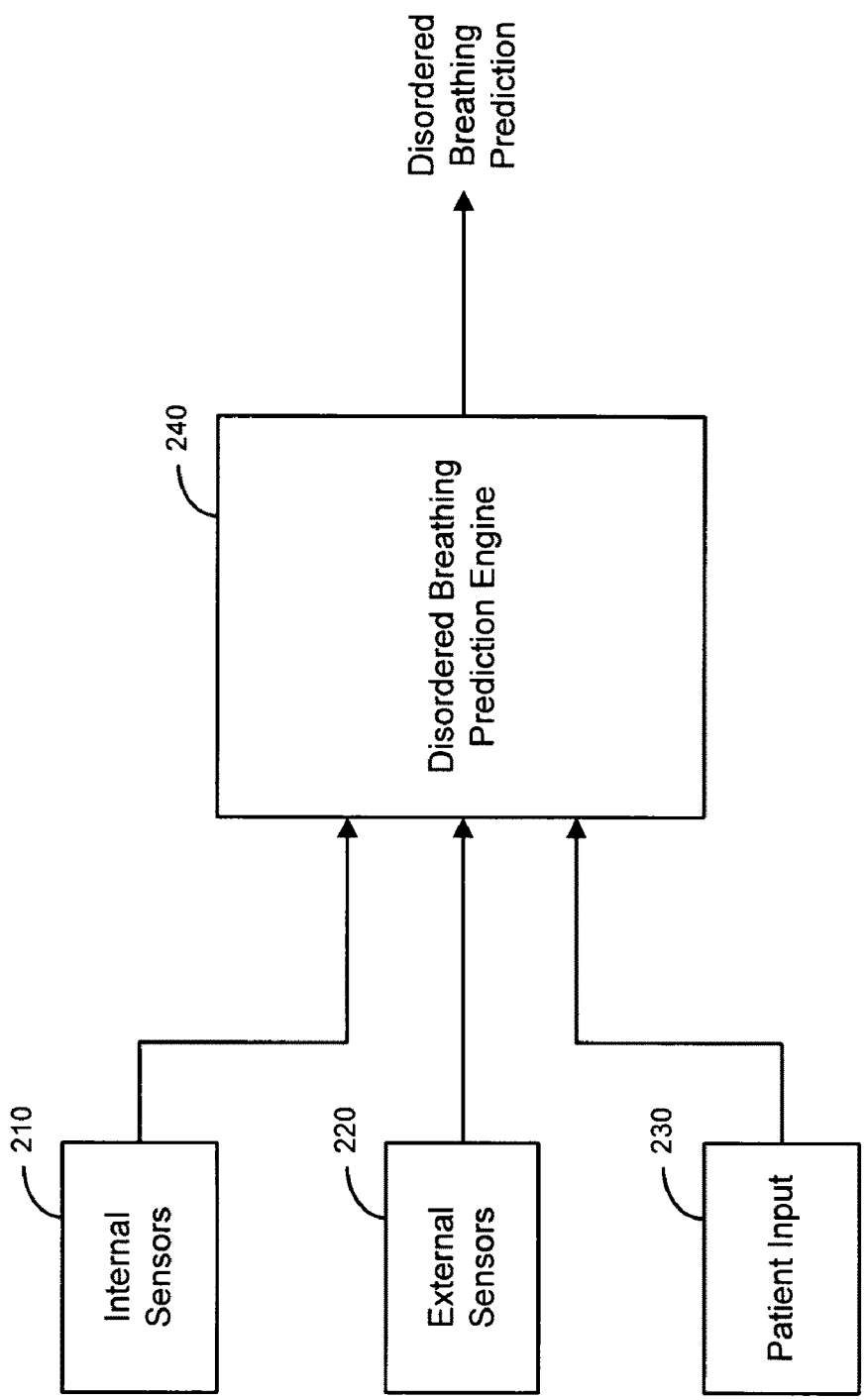
FIG. 2 is a block diagram of a system for predicting disordered breathing in accordance with embodiments of the invention.

FIG. 2 illustrates a block diagram of a system for detecting conditions associated with disordered breathing and predicting disordered breathing in accordance with embodiments of the invention. The system may use internal sensors 210, implanted within the body of the patient, to detect physiological conditions affecting the patient. For example, the system may detect heart rate, tidal volume, and/or other physiological signals using an intracardiac electrocardiogram (EGM) signal detector and transthoracic impedance sensor that are part of an implanted cardiac rhythm management system such as a cardiac pacemaker or defibrillator.

The system may further use external sensors 220 and detect physiological or contextual conditions using signals from the external sensors 220. In one scenario whether the patient is snoring may be useful in predicting disordered breathing. Snoring noises may be sensed using an external microphone or an implanted accelerometer. Signals representing the snoring noises may be transmitted from the sensors to the system and used to detect that the patient is snoring. In another situation, temperature and humidity may be factors in the patient's disordered breathing. Signals from temperature and humidity sensors may be used to aid in the prediction of disordered breathing.

Additionally, the system may use information input 230 by the patient to inform the disordered breathing prediction system of patient conditions. In various embodiments, the patient's medical history, self-described medication use, alcohol or tobacco use, day-time sleepiness, or perceptions of sleep quality over the past few nights may be useful in connection with the disordered breathing prediction.

Signals from one or more of the internal sensors 210, external sensors 220, and patient input 230 may be coupled to a disordered breathing prediction engine 240 for prediction analysis. In one example, the conditions associated with disordered breathing may be sensed and processed using implantable sensors 210 and the prediction analysis performed by an external disordered breathing prediction engine 240. Some or all of the implantable sensors 210 may have remote communication capabilities, such as a wireless proprietary or a wireless Bluetooth communications link. The wireless communications link couples the implantable sensor or sensors 210 to the external disordered breathing prediction engine 240. Electrical signals representing conditions associated with disordered breathing are produced by the implantable sensors 210 and transmitted to the external disordered breathing prediction engine 240.

In another example, a disordered breathing prediction system is configured to include an implantable therapy device incorporating a disordered breathing prediction engine 240 and one or more external sensors 220. Signals representing the detected conditions may be transmitted from the external sensors to the prediction engine 240 over a wireless communication link. The above examples provide only a few of the many possible configurations that may be used to predict disordered breathing.

In yet another example, internal sensors 210 may be coupled to an internal prediction engine 240 using a lead system. Various combinations of internal sensors 210, external sensors 220, and patient input devices 230 coupled through wireless or wired connections to the prediction engine 240 are possible.

Each of the conditions listed in Table 1 may serve a variety of purposes in predicting disordered breathing. Various subsets of the conditions listed in Table 1 may be detected as predisposing conditions, precursor conditions, and/or verification conditions useful in the prediction of disordered breathing. In one example, information regarding sleep onset may be employed in prediction of sleep disordered breathing. A subset of the conditions listed in Table 1 may be used to detect whether the patient is asleep and to track the various stages of sleep. Another subset of the conditions may be employed to detect and classify disordered breathing episodes. Table 2 below provides further examples of how the physiological and contextual conditions of the patient may be used in disordered breathing prediction.

TABLE 2

| Condition | Examples of how condition is used in disordered breathing prediction |
| --- | --- |
| Heart rate | Decrease in heart rate may indicate disordered breathing episode. |
| | Decrease in heart rate may indicate the patient is asleep. |
| Heart rate variability | May be used to determine sleep state |
| Ventricular filling pressure | May be used to identify/predict pulmonary congestion associated with respiratory disturbance. |
| Blood pressure | Swings in on-line blood pressure measures are associated with apnea. |
| Snoring | Snoring is associated with a higher incidence of obstructive sleep apnea and may be used to detect disordered breathing. |
| Respiration signals/respiration patterns | Respiration patterns may be used to detect disordered breathing episodes. |
| | Respiration patterns may be used to determine the type of disordered breathing. |
| | Respiration patterns may be used to detect that the patient is asleep. |
| | Hyperventilation may be used to predict disordered breathing. |
| | Previous episodes of disordered breathing may be used to predict further episodes. |
| | One form of disordered breathing may be used to predict another form of disordered breathing |
| Patency of upper airway | Patency of upper airway is related to obstructive sleep apnea and may be used to detect episodes of obstructive sleep apnea. |
| Pulmonary congestion | Pulmonary congestion is associated with respiratory disturbances. |
| Sympathetic nerve activity | End of apnea associated with a spike in SNA |
| CO2 saturation | Low CO2 levels initiate central apnea. |
| O2 saturation | O2 desaturation occurs during severe apnea/hypopnea episodes. |
| Blood alcohol content | Alcohol tends to increase incidence of snoring & obstructive apnea. |
| Adrenalin | End of apnea associated with a spike in blood adrenaline. |
| BNP | A marker of heart failure status, which is associated with Cheyne-Stokes Respiration |
| C-Reactive Protein | A measure of inflammation that may be related to apnea. |
| Drug/Medication/Tobacco use | These substances may affect incidence of both central & obstructive apnea. |
| Muscle atonia | Muscle atonia may be used to detect REM and non-REM sleep. |
| Eye movement | Eye movement may be used to detect REM and non-REM sleep. |

TABLE 2-continued

| Condition | Examples of how condition is used in disordered breathing prediction |
| --- | --- |
| Temperature | Ambient temperature may be a condition predisposing the patient to episodes of disordered breathing. |
| Humidity | Humidity may be a condition predisposing the patient to episodes of disordered breathing. |
| Pollution | Pollution may be a condition predisposing the patient to episodes of disordered breathing. |
| Posture | Posture may be used to determine if the patient is asleep. Posture may be a condition predisposing the patient to episodes of disordered breathing. |
| Activity | Patient activity may be used in relation to sleep detection. |
| Sleep stage | NREM sleep is associated with a higher incidence of DB episodes |
| Location | Patient location may used to determine if the patient is in bed as a part of sleep detection. |

Figure 3:
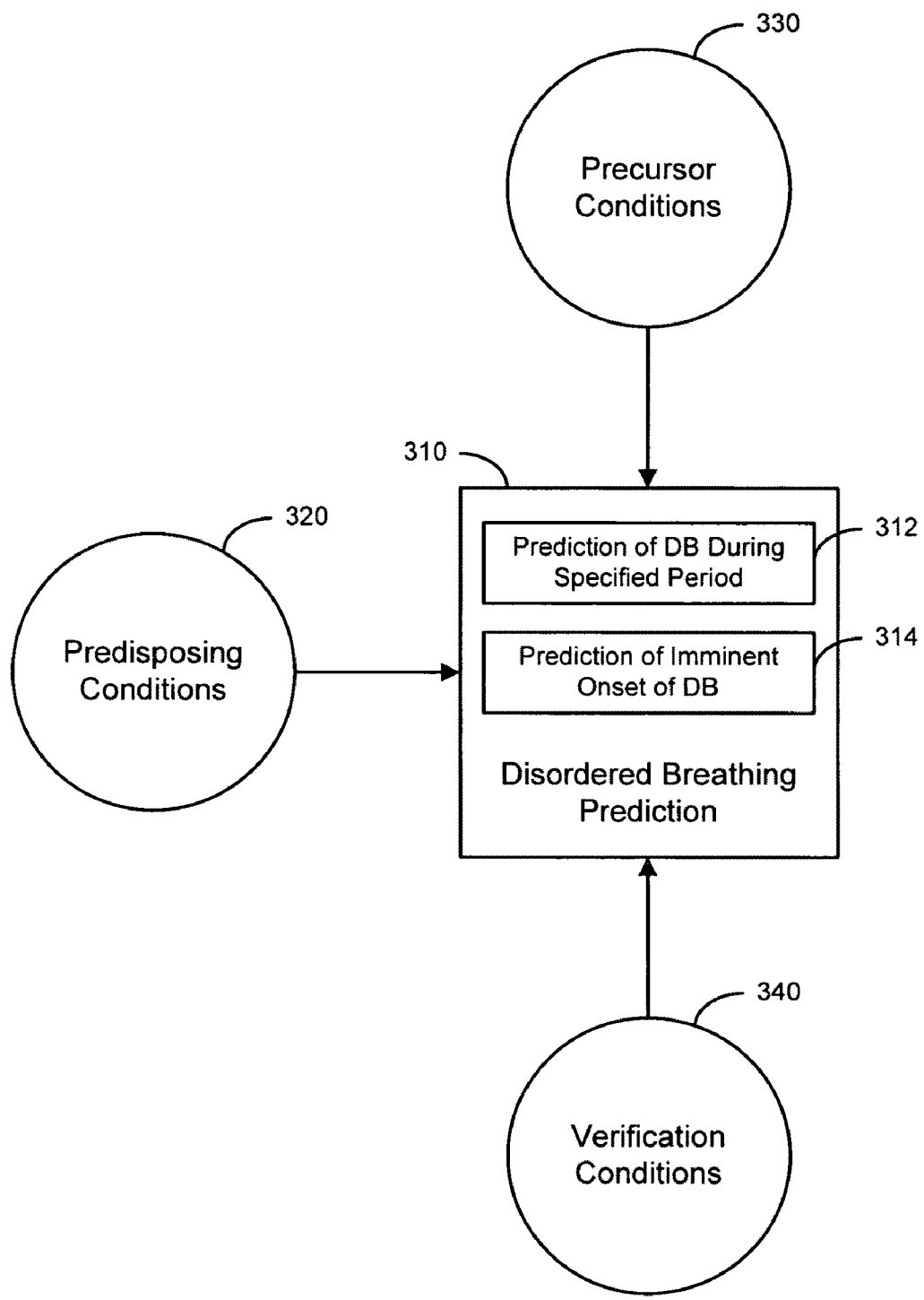
FIG. 3 illustrates conditions that are used to predict disordered breathing according to embodiments of the invention.

FIG. 3 conceptually illustrates how conditions such as those listed in Table 1 and/or 2 may be used in predicting disordered breathing 310 according to embodiments of the invention. In one embodiment, the system tracks one or more of the conditions listed in Table 1 and/or 2 to predict disordered breathing. For example, over the course of a period of time, e.g., at least about a 16 hour window preceding and including the patient's historical sleep time, the system may track one or more conditions to determine the presence and/or level of each particular condition.

In one implementation, the system tracks conditions that have been determined to predispose 320 the patient to an attack of disordered breathing. Predisposing conditions represent conditions statistically associated with an onset of disordered breathing. Prediction of disordered breathing based on predisposing conditions may be performed in real-time. The presence of one or more predisposing conditions consistent with prediction criteria may indicate that disordered breathing is likely to occur within the next time period, such as during the current sleep period, or during the next time period of about eight hours. For example, the conditions predisposing the patient to disordered breathing may include the air pollution index of the patient's environment downloaded from an air quality website, recent tobacco use reported by the patient, the degree of the patient's pulmonary congestion detected by an implanted transthoracic impedance sensor, as well as other internally or externally detected predisposing conditions.

Additionally, or alternatively, the system may use previous episodes of disordered breathing to determine that the patient is predisposed to further episodes of disordered breathing within particular time period, such as during the night. For example, previous episodes of disordered breathing during a first interval within a sleep period may be an indication that additional episodes are likely to occur in a second and subsequent interval within the same sleep period. Therefore, the system may use the type, duration, frequency, and severity of the previous disordered breathing episodes to inform the disordered breathing prediction analysis.

The occurrence of one type of disordered breathing may predict another type. For example, the occurrence of obstructive sleep apnea episodes may be used to predict that central sleep apnea will occur later during the night. In another example, the occurrence of a hypopnea episode may be used to predict an apnea episode. Quantification of the severity, frequency, and duration of disordered breathing may be accomplished using any of a number of disturbed breathing measures, including, for example, percent time in disordered breathing and the apnea/hypopnea index.

A further example of a condition predisposing a patient to hypopnea or apnea is body posture. A supine posture is more likely to result in obstruction of the upper airway and can be used to predict episodes of obstructive hypopnea and apnea. Posture sensing may be implemented using a position sensitive switch coupled to the patient. Posture and/or torso orientation sensing may be accomplished, for example, using an implantable or external multiaxis accelerometer.

The patient's location may also be useful in prediction of disordered breathing. Because disordered breathing often occurs during sleep, the patient may be more likely to experience disordered breathing if the patient is in bed. A bed proximity sensor may be implemented by placing a beacon transmitter on the patient's bed. Receiver circuitry on or in the patient, for example, incorporated in the patient's pacemaker, receives the beacon signal and determines that the patient is in bed. A proximity to bed sensor methodology is further described in commonly owned U.S. Pat. No. 7,400,928.

Conditions that predispose the patient to disordered breathing 320 are conditions that, if detected, indicate the likelihood that one or more episodes of disordered breathing will occur during the next time period, such as over the course of the night. Based on predisposing conditions 320, an onset of disordered breathing may be predicted 312 to occur within a time window that may include several hours, for example. A second set of factors, denoted herein as precursor conditions 330, may be used to predict 314 an impending onset of disordered breathing. Precursor conditions 330 indicate that an episode of disordered breathing is imminent. Prediction of disordered breathing may be performed in real-time. The presence of precursor conditions consistent with prediction criteria may be used to predict that disordered breathing will occur within a time window that may be measured in terms of minutes or seconds, for example, within about the next five minutes.

Precursor conditions 330 indicative of an impending onset of disordered breathing may include, for example, pre-apnea or pre-hypopnea conditions. In one embodiment, decreased levels of $CO_2$ in a particular patient may be causal to central apnea. Therefore, a condition of pre-apnea may be detected when a patient's $CO_2$ level, as measured by an external $CO_2$ sensor, falls below a selected level, indicating the impending onset of an apnea episode.

In another embodiment, a patient's heart rate variability may be significantly altered before, during, and after episodes of apnea. Heart rate variability may be used, for example, as a precursor condition to predict an impending episode of disordered breathing.

In yet another embodiment of the invention, a pre-disordered breathing condition, e.g., pre-apnea or pre-hypopnea, may be detected by analyzing the patient's respiration patterns or the morphology of a respiration signal. Respiration cycles just prior to an apnea event may exhibit a characteristic pattern. For example, an apnea event for many patients is preceded by a period of hyperventilation with a number of rapid, deep breaths. The pattern of hyperventilation may be detected by analyzing patient's transthoracic impedance signal to determine respiration rate and tidal volume.

Cheyne-Stokes respiration and some apnea/hypopnea episodes may exhibit a crescendo-decrescendo respiration pattern. The crescendo-decrescendo respiration pattern produces hyperventilation during the crescendo stage and hypoventilation during the decrescendo phase. Hyperventilation, secondary to pulmonary congestion, drives arterial partial pressure of carbon dioxide down. A decrease in arterial partial pressure of carbon dioxide below an apnea level may be a causal mechanism for central apnea. According to one embodiment of the invention, detection of an impending onset of disordered breathing may be implemented by detecting a series of increasing tidal volumes followed by a series of decreasing tidal volumes.

For some patients, disordered breathing occurs at regular intervals, allowing the periodicity of the disordered breathing episodes to be used as a precursor condition. If disordered breathing episodes of the patient occur at regular intervals, the next episode of disordered breathing may be predicted based on the time elapsed since the last episode was detected. Precursor conditions 330 may be analyzed individually, or in combination with one or more predisposing conditions 320, to predict the impending onset of a disordered breathing episode.

Snoring is an example of a pre-apnea or pre-hypopnea condition. In many, patient snoring, or more generally any abnormal airflow in the upper airway detectable via acoustic means, precedes more significant sleep disordered breathing conditions such as hypopnea or apnea.

Yet another group of conditions may be used to verify a prediction of disordered breathing. For example, after a prediction of disordered breathing is made, one or more verification conditions 340 may be checked to confirm the prediction. The verification conditions, as well as the physiological and contextual conditions used in the first stage of the prediction analysis, may be highly patient specific.

In one example, a characteristic pattern of respiration is a reliable predictor of disordered breathing in a particular patient only when the patient is supine. If the prediction is made while the patient not supine, normal variations in respiration cycles in this particular patient may lead to an erroneous prediction of disordered breathing. Thus, before disordered breathing is predicted, the posture sensor signal is checked to verify that the patient is supine. If the patient is supine and the patient's respiration cycles are consistent with criteria indicating that disordered breathing is likely, the prediction may be made.

In another example, the patient is known to suffer from episodes of apnea during sleep. The patient's sleep apnea may be predicted using a number of physiological and contextual conditions. The prediction of sleep apnea may be made after assessing that the patient's posture and location are consistent with sleep.

Before a prediction of sleep apnea is made, the system confirms that the patient is lying down in bed by checking the signal from an implantable posture sensor and a bed proximity sensor.

Alternatively, or additionally, the system may detect that the patient is sleeping by examining the patient's respiration and/or activity prior to making a prediction regarding sleep disordered breathing. A method for determining that the patient is asleep is described in commonly owned U.S. Pat. No. 7,189,204, which is incorporated herein by reference in its entirety.

Episodes of disordered breathing are associated with acute physiological effects, including, for example, negative intrathoracic pressure, hypoxia, and arousal from sleep. During obstructive apnea, for example, the effort to generate airflow increases. Attempted inspiration in the presence of an occluded airway result in an abrupt reduction in intrathoracic pressure. The repeated futile inspiratory efforts associated with obstructive sleep apnea may trigger a series of secondary responses, including mechanical, hemodynamic, chemical, neural, and inflammatory responses.

Obstructive sleep apneas are terminated by arousal from sleep several seconds after the apneic peak, allowing the resumption of airflow. Coincident with arousal from sleep, surges in sympathetic nerve activity, blood pressure, and heart rate occur. The adverse effects of obstructive apnea are not confined to sleep. Daytime sympathetic nerve activity and systemic blood pressure may be increased. There may also be a sustained reduction in vagal tone, causing reduction in total heart rate variability during periods of wakefulness.

Central sleep apnea is generally caused by a failure of respiratory control signals from the brain and is a component of Cheyne-Stokes respiration (CSR), a respiration pattern primarily observed in patients suffering from chronic heart failure (CHF). Cheyne-Stokes respiration is a form of periodic breathing in which central apneas and hypopneas alternate with periods of hyperventilation causing a waxing-waning pattern of tidal volume. In some patients, obstructive sleep apnea and central sleep apnea may coexist. In these patients, there is generally a gradual shift from predominantly obstructive apneas at the beginning of the night to predominantly central apneas at the end of the night.

When CHF patients lie down, the prone posture may create central fluid accumulation and pulmonary congestion causing the patient to reflexively hyperventilate. Central apnea is usually initiated during sleep by an increase in ventilation and a reduction of arterial partial pressure of carbon dioxide ($PaCO_2$) that is triggered by spontaneous arousal. When $PaCO_2$ falls below the threshold level required to stimulate breathing, the central drive to the respiratory muscles and airflow cease, and central apnea ensues. Apnea persists until $PaCO_2$ rises above the threshold required to stimulate ventilation.

Arousals are not required in central sleep apneas for the resumption of breathing at the termination of the apneic event. In central apnea, the arousals follow the initiation of breathing and facilitate the development of oscillations in ventilation by recurrently stimulating hyperventilation and reducing $PaCO_2$ below the apneic threshold. Once triggered, the pattern of alternating hyperventilation and apnea is sustained by the combination of increased respiratory drive, pulmonary congestion, arousals, and apnea-induced hypoxia causing $PaCO_2$ oscillations above and below the apneic threshold. Shifts in the patient's state of consciousness, particularly with repeated arousals, may further destabilize breathing.

With the transition from wakefulness to NREM sleep the waking neural drive to breathe is lost, and the threshold for a ventilatory response to $CO_2$ is increased. Therefore, if the patient's $PaCO_2$ level during wakefulness is below this higher sleeping threshold, the transition to NREM sleep may be accompanied by a transient loss of respiratory drive resulting in a central apnea. During the apnea, the $PaCO_2$ rises until it reaches the new higher threshold level and initiates breathing.

If sleep becomes firmly established, regular breathing resumes. However, if an arousal should occur, the increased $PaCO_2$ level associated with sleep is now relatively too high for a state of wakefulness and will stimulate hyperventilation. Thus, although arousals terminate obstructive sleep apneas, arousals may trigger the respiratory oscillations associated with central apneas, particularly Cheyne-Stokes respiration.

In addition to the acute responses to central sleep apnea discussed above, central sleep apnea is also associated with a number of secondary responses, including, for example, decreased heart rate variability (HRV), and blood pressure changes. Patients with central sleep apnea may have higher urinary and circulating norepinephrine concentrations and lower $PaCO_2$ during both sleep and wakefulness.

Figure 4:
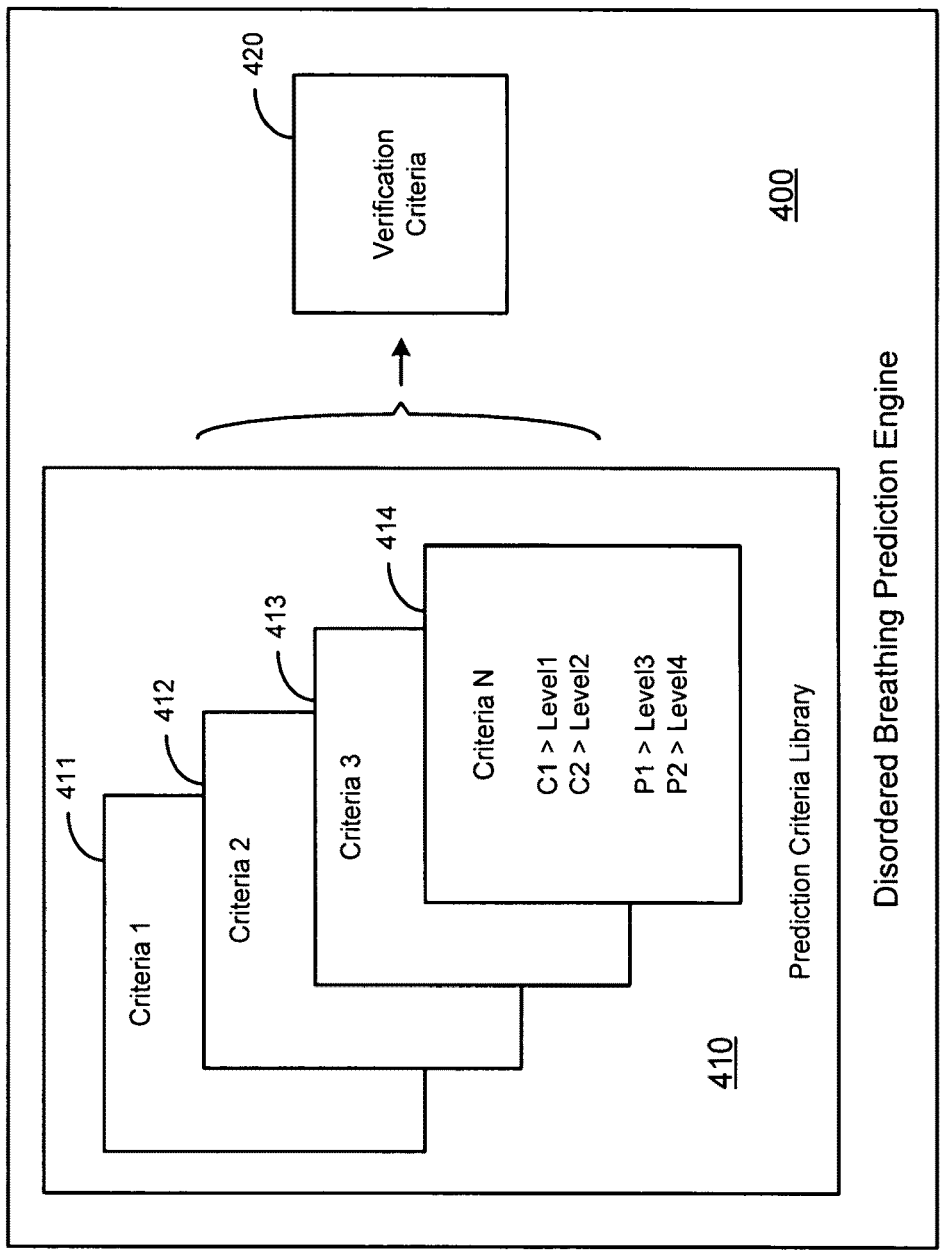
FIG. 4 is a block diagram of a disordered breathing prediction engine in accordance with embodiments of the invention.

The operation of a disordered breathing prediction engine 400, according various to embodiments, is conceptually illustrated in the block diagram of FIG. 4. Periodically, one or more conditions are detected and compared to a library 410 of prediction criteria. The prediction criteria library 410 may incorporate one or more sets of prediction criteria 411, 412, 413, 414. Each of these sets of criteria may be compared to the detected conditions. If the criteria of a prediction criteria set 411, 412, 413, 414 are substantially consistent with the detected conditions, a preliminary disordered breathing prediction may be made.

In various embodiments, the prediction criteria sets 411, 412, 413, 414 represent one or more condition thresholds associated with an onset of disordered breathing. In one embodiment, the level of one or more conditions may be compared to the prediction criteria sets 411, 412 413, 414. If the levels of the one or more conditions are substantially equal to or greater than the thresholds specified in a prediction criteria set 411, 412, 413, 414, a preliminary prediction of disordered breathing is made.

The example above and the examples that follow are described in terms of a condition being consistent with a prediction criteria when the condition exceeds a prediction criteria threshold. However, it will be understood by those skilled in the art that different threshold requirements may be defined for different conditions. For example, one condition may be defined to be consistent with a prediction criterion when the condition exceeds a prediction criterion threshold. Another condition may be defined to be consistent with a prediction criterion threshold when the condition falls below the threshold. In yet another example, a condition may be defined to be consistent with the prediction criterion when the condition falls within a specified range of values. A detected condition may be consistent with a particular prediction criteria in terms of a timing, a rate of change or a maximum or minimum value of the condition, for example.

In the example provided in FIG. 4, the prediction criteria N 414 involves two contextual conditions, C1 and C2, and two physiological conditions, P1 and P2. In this particular example, if conditions C1, C2, P1, and P2 exceed levels Level1, Level2, Level3, and Level4, respectively, the patient is likely to experience disordered breathing during the night. Therefore, when conditions C1, C2, and P1, P2 reach the levels specified in criteria N 414, preliminary prediction of disordered breathing is made.

In another embodiment of the invention, the relationships between the detected conditions are analyzed to predict disordered breathing. In this embodiment, the disordered breathing prediction may be based on the existence and relative values associated with two or more conditions. For example, if condition A is present at a level of x, then condition B must also be present at a level of f(x) before a disordered breathing prediction is made.

In yet another embodiment of the invention, the estimated probability, $P(C_n)$, that disordered breathing will occur if a particular condition level is detected may be expressed as a function of the ratio of the number of times disordered breathing occurred within a selected time interval following the detection of the particular condition level to the total number of observed occurrences of the condition level. The probability that disordered breathing will occur, $P(C_n)$, is compared to a threshold probability level to make the disordered breathing prediction. Other methods of calculating the estimated probability are also possible.

The prediction of disordered breathing may be based on the convergence or divergence of a number of conditions occurring within the same time period. In this situation, a composite probability score may be computed as a combination of the individual probabilities. In one embodiment, the probabilities are combined by adding the condition probabilities after multiplying each of the condition probabilities by a weighting factor. For example, if the disordered breathing prediction is based on four substantially simultaneous conditions, $C_1$, $C_2$, $C_3$, and $C_4$, the total probability score $PS_T$ may be calculated as:

$$PS_T = A \times P(C_1) + B \times P(C_2) + C \times P(C_3) + D \times P(C_4), \qquad [1]$$

where A, B, C, and D are scalar weighting factors that may be used to estimate the relative importance of each of the conditions $C_1$, $C_2$, $C_3$, and $C_4$. If the probability score exceeds a selected prediction criteria threshold, then disordered breathing is predicted.

Although the above process describes combining the estimated probabilities for each condition by adding each of the estimated probabilities, other methods are also possible. For example, a detected condition may operate against a prediction of disordered breathing. In this situation, the estimated probability, $P_n(C_n)$, that disordered breathing will not occur if a particular condition level is detected may be expressed as a function of the ratio of the number of times disordered breathing did not occur within a selected time interval following the detection of the particular condition level to the total number of observed occurrences of the condition level. This value may be subtracted from the total to determine the probability score. Non-linear methods of combining the estimated probabilities to arrive at a composite probability are also possible.

If the conditions affecting the patient are consistent with a prediction of disordered breathing, the prediction may be verified by comparing one or more verification conditions to verification criteria. If the verification conditions are consistent with the verification criteria, a prediction of disordered breathing is made.

In the embodiments described above, predictions of disordered breathing are based upon comparisons of one or more detected conditions to sets of prediction criteria. The initial data from which the initial prediction criteria sets are formed may be derived from past observations taken from population data, or from data collected from a particular patient. The initial prediction criteria sets may then be modified as additional data are collected from the patient.

In one embodiment, an estimated accuracy for the prediction criteria is updated for every prediction event. The estimated positive predictive value (PPV) for a prediction criteria set N may be expressed as:

$$PPV_N = \frac{TP}{TP + FP} \qquad [2]$$

where TP (true positive) is the number of times the prediction criteria set successfully predicted disordered breathing, and FP (false positive) is the number of times the prediction criteria erroneously predicted disordered breathing.

If the estimated accuracy of prediction criteria set N, $PPV_N$, falls below a predetermined level, for example, 0.7, the prediction criteria set N may be modified. In one embodiment, a possible prediction criteria set is formed, for example, by modifying the threshold level of one or more of the conditions represented by the original prediction criteria set N. In one embodiment, each threshold in the original prediction criteria set N is modified by an incremental value, to make the prediction criteria set more accurate.

In another embodiment, conditions represented in the original prediction criteria set N are compared to the conditions that are present just prior to a disordered breathing occurrence to determine how the modification for the possible prediction criteria set should be implemented. For example, if the level of a particular condition just prior to the occurrence shows a relatively large variation just prior to the disordered breathing episode, but the levels of other conditions remain constant, then only the changing level may be modified in the possible prediction criteria set.

Each time the possible prediction criteria set is satisfied, no prediction of disordered breathing is made, however, the accuracy of the possible prediction criteria set is updated, for example, using an equation similar in form to Equation 2. If the accuracy of the possible prediction criteria set reaches a selected level, for example, 0.7, and the accuracy original prediction criteria set N remains below 0.7, the possible prediction criteria set may replace the original prediction criteria set N in the prediction criteria library.

According to various embodiments, new prediction criteria sets may be added to the prediction criteria library. In accordance with these embodiments, if a disordered breathing episode occurs without prediction, the levels of the detected conditions prior to the disordered breathing episode are saved as a possible prediction criteria set. Each time the possible prediction criteria set is satisfied, no prediction of disordered breathing is made, however, the accuracy of the possible prediction criteria set is updated, for example, using an equation similar in form to Equation 2. If the accuracy of the possible prediction criteria set reaches a selected level, for example, 0.7, the possible prediction criteria set may be added to the prediction criteria library.

The system may also be adjusted to provide increasingly sensitive disordered breathing prediction criteria sets, according to various embodiments. The estimated sensitivity for a prediction criteria set N may be expressed as:

$$Sensitivity_N = \frac{TP}{TP + FN} \quad [3]$$

where TP (true positive) is the number of times the prediction criteria successfully predicted disordered breathing, and FN (false negative) is the number of times the prediction criteria erroneously predicted that disordered breathing would not occur.

In one embodiment, if the prediction criteria accuracy for the prediction criteria set N becomes larger than a selected number, for example, 0.9, then the threshold levels of one or more of the conditions represented in the prediction criteria set N may be adjusted to provide enhanced sensitivity.

In one example, the threshold level of each condition represented in the prediction criteria set N is modified by an incremental value, thus making the prediction criteria set N more sensitive. In another embodiment, conditions represented in the prediction criteria set N are compared to the conditions that are present just prior to a disordered breathing occurrence to determine how the modification of the prediction criteria set N should be implemented. In yet another embodiment, a condition threshold level that is modified is based upon the relative importance of the condition in the overall prediction criteria. In another example, if the level of a particular condition is changing just prior to the occurrence of the disordered breathing episode, but the levels of other conditions remain constant, only the changing condition may be modified.

Following adjustment by any of the processes described above, the adjusted prediction criteria set may be designated as possible prediction criteria set. Each time the possible prediction criteria set is satisfied, no prediction of disordered breathing is made, however, the accuracy of the possible prediction criteria set is updated, for example, using Equation 2 or 3. If the accuracy of a possible prediction criteria set reaches a selected level, for example, 0.7, the possible prediction criteria set may be added to the prediction criteria library.

The system may also be adjusted to provide improved specificity or negative predictive value (NPV) of disordered breathing prediction criteria in a manner similar to the adaptive method described previously. Calculation of specificity and NPV for a prediction criteria N may be accomplished using equations 4 and 5 below.

$$Specificity_N = \frac{TN}{TN + FP} \quad [4]$$

$$NPV_N = \frac{TN}{TN + FN} \quad [5]$$

where TN (true negative) is the number of times the prediction criteria successfully predicted the absence of disordered breathing, FP (false positive) is the number of times the prediction criteria erroneously predicted disordered breathing and FN (false negative) is the number of times the prediction criteria erroneously predicted the absence of disordered breathing.

Figure 5:
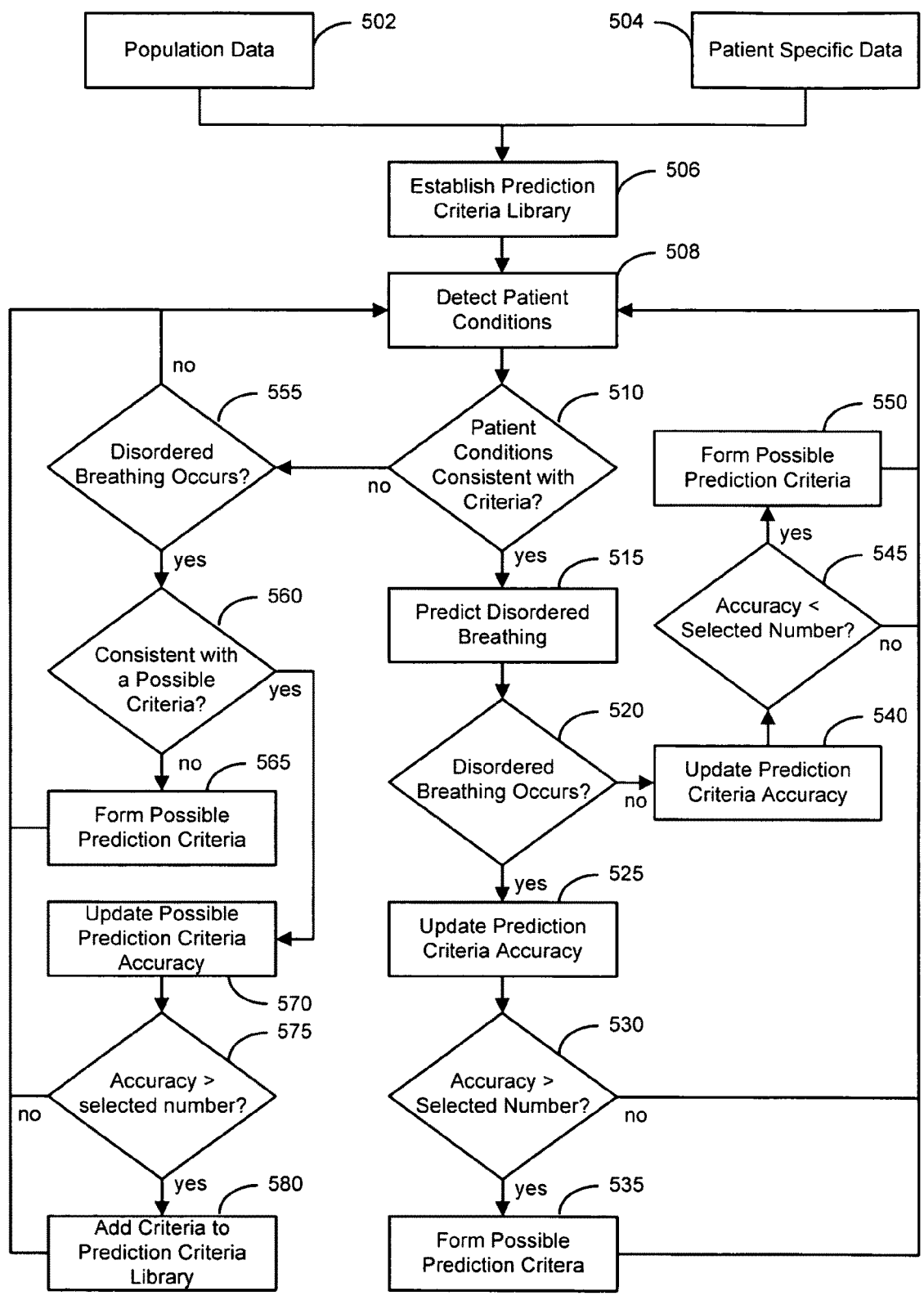
FIG. 5 is a flow graph illustrating a method of updating a prediction criteria library according to embodiments of the invention.

The flowchart of FIG. 5 illustrates a method for establishing and updating the prediction criteria library according to embodiments of the invention. Previous observations of disordered breathing may be assimilated from population data 502 or from past observation of the specific patient 504. One or more prediction criteria sets are determined and organized in a prediction criteria library 506.

Conditions associated with disordered breathing are periodically detected 508 and compared to the prediction criteria sets in the prediction criteria library. If the levels of the detected conditions are consistent 510 with any of the prediction criteria sets in the library, then disordered breathing is predicted 515. Within a time window following the disordered breathing prediction, the system determines if disordered breathing occurs 520.

One method for detecting disordered breathing involves monitoring a respiratory waveform output, for example, using a transthoracic impedance sensor. When the tidal volume (TV) of the patient's respiration, as indicated by the transthoracic impedance signal, falls below a hypopnea threshold, then a hypopnea event is declared. For example, a hypopnea event may be declared if the patient's tidal volume fall below about 50% of the recent average tidal volume or other baseline tidal volume. When the patient's tidal volume falls further to an apnea threshold, e.g., about 10% of the recent average tidal volume, an apnea event is declared.

Another method for detecting disordered breathing involves defining and analyzing a number of respiratory cycle intervals. Such a method is described in commonly owned U.S. Pat. No. 7,252,640, which is incorporated herein by reference in its entirety.

If disordered breathing occurs 520, the prediction criteria accuracy of the prediction criteria set used for the disordered breathing prediction is updated 525. If the updated prediction criteria accuracy is greater 530 than a selected number, then a possible prediction criteria set is formed 535. The possible prediction criteria set may be formed, for example, by substituting more sensitive condition levels when compared to the original prediction criteria set.

If disordered breathing is not detected 520 following the prediction, then the prediction criteria set accuracy is updated 540. If the prediction criteria set accuracy decreases 545 below a selected number, then a possible prediction criteria set 550 is formed. The possible prediction criteria set may be formed, for example, by substituting more stringent condition levels to produce a more accurate prediction.

If the detected conditions are not consistent 510 with any of the prediction criteria sets in the prediction criteria library, disordered breathing is not predicted. Within a time window following the disordered breathing prediction, the system determines if disordered breathing occurs 555. If disordered breathing occurs 555, then the system checks to see if the conditions are consistent 560 with any of the possible prediction criteria sets. If the conditions are not consistent 560 with any of the possible prediction criteria sets, a possible prediction criteria set is formed 565.

If the conditions are consistent 560 with a possible criteria set, the possible prediction criteria set accuracy is updated 570. If the possible prediction criteria accuracy increases beyond a selected number 575, the possible prediction criteria set is added 580 to the prediction criteria library.

Figure 6:
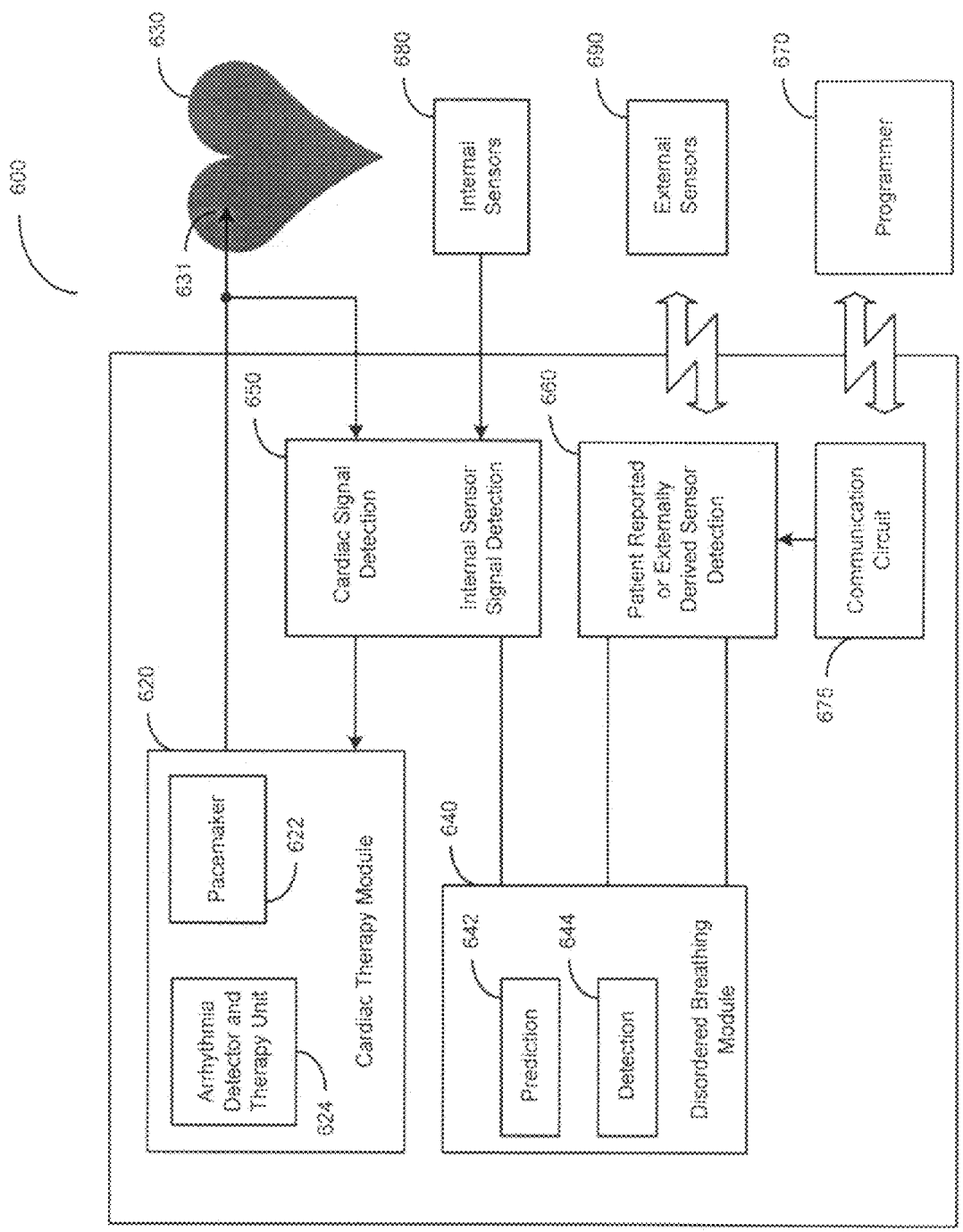
FIG. 6 is a block diagram of a cardiac rhythm management system incorporating a disordered breathing prediction engine in accordance with embodiments of the invention.

The block diagram of FIG. 6 illustrates a system for predicting disordered breathing configured in accordance with embodiments of the invention. According to one embodiment, a disordered breathing prediction engine 642 is incorporated within a cardiac rhythm management system 600. The cardiac rhythm management system may include, for example, a cardiac therapy module 620 including a pacemaker 622 and an arrhythmia detector/therapy unit 624. The cardiac therapy module 620 is coupled to a lead system having electrodes 631 implanted to electrically couple the heart 630 to the cardiac rhythm management system 600.

The cardiac rhythm management system 600 includes circuitry 650 for detecting signals from internal sensors such as the implanted cardiac electrodes 631, and other internal sensors 680 such as the internal sensors listed in Table 1. The internal sensors 680, may be coupled to the implanted signal detection circuitry 650 through conducting leads as shown, or through a wireless connection, for example.

The cardiac rhythm management system 600 may also include circuitry 660 for detecting signals from external sensors 690 located outside the patient's body and from patient reported input. The external sensors 690 may be coupled to the detection circuitry 660 through a wireless link. Signals representing patient reported data may be input through a programmer unit 670 that is wirelessly coupled to a telemetry circuit 675 within the cardiac rhythm management system 600.

The cardiac therapy module 620 receives cardiac signals from the implanted cardiac electrodes 631 and analyzes the cardiac signals to determine an appropriate therapy. The cardiac therapy may include pacing therapy controlled by the pacemaker 622 to treat cardiac rhythms that are too slow. The pacemaker 622 controls the delivery of periodic low energy pacing pulses to one or more of the heart chambers through cardiac electrodes 631 to ensure that the periodic contractions of the heart are maintained at a hemodynamically sufficient rate.

The cardiac therapy may also include therapy to terminate tachyarrhythmia, wherein the heart rate is too fast. The arrhythmia detector/therapy unit 624 detects and treats episodes of tachyarrhythmia, including tachycardia and/or fibrillation. The arrhythmia detector/therapy unit 624 recognizes cardiac signals indicative of tachyarrhythmia and delivers high energy stimulations to the heart 630 through the implanted electrodes 631 to terminate the arrhythmia.

A disordered breathing module 640 incorporated within the cardiac rhythm management system 600 includes circuitry for disordered breathing detection 644, as well as the disordered breathing prediction engine 642. The implanted signal detection circuitry 650 and patient reported/external sensor detection circuitry 660 are coupled to the disordered breathing module 640. The implanted signal detection circuitry 650 and patient reported/external sensor detection circuitry 660 provide signals associated with various conditions used for disordered breathing detection and prediction. A prediction of disordered breathing by the disordered breathing prediction engine 642 may be used to trigger cardiac pacing therapy delivered by the cardiac therapy module to mitigate disordered breathing as more fully described in commonly owned U.S. Pat. No. 7,680,537, incorporated herein by reference in its entirety.

Although the disordered breathing prediction engine 642 is described in connection with FIG. 6 as a component of an implantable cardiac rhythm management system, the disordered breathing prediction engine 642 may be incorporated in various implantable or external therapeutic or diagnostic devices including cardiac monitors, pacemakers, defibrillators, and cardiac resynchronizers, for example.

Figure 7:
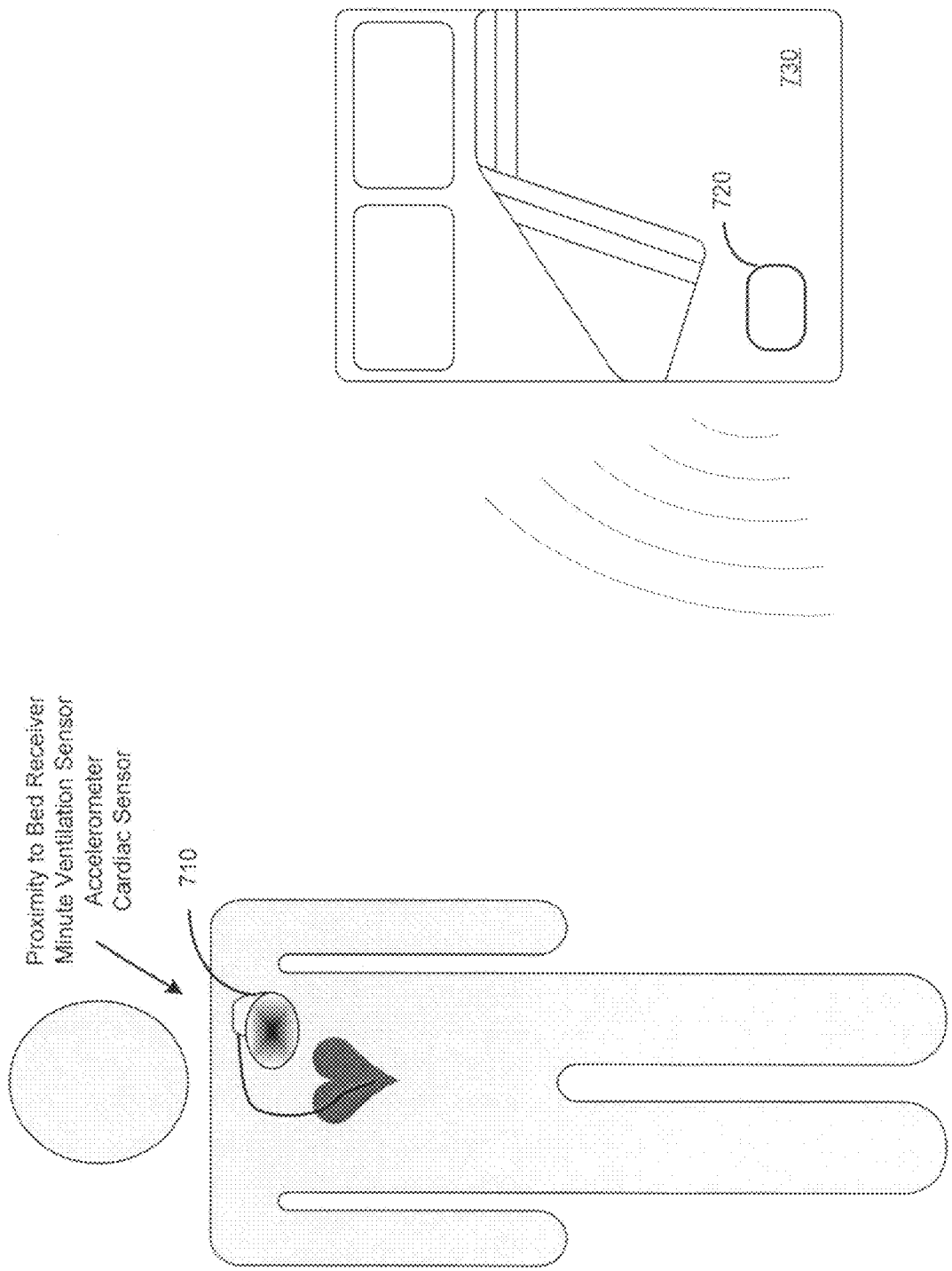
FIG. 7 is a diagram illustrating a system for predicting disordered breathing in accordance with embodiments of the invention.
Figure 8A:
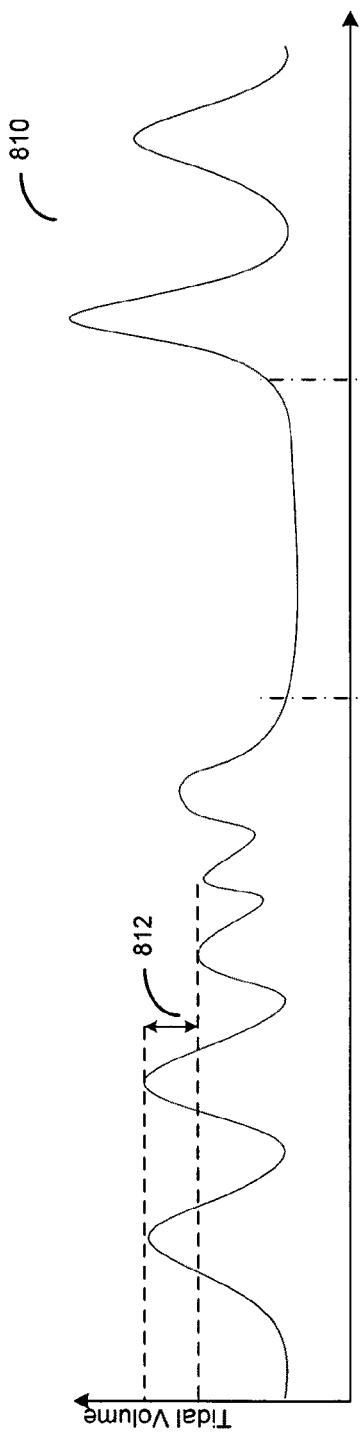
FIG. 8A illustrates a representative graph of tidal volume signal used in connection with disordered breathing prediction in accordance with embodiments of the invention.
Figure 8B:
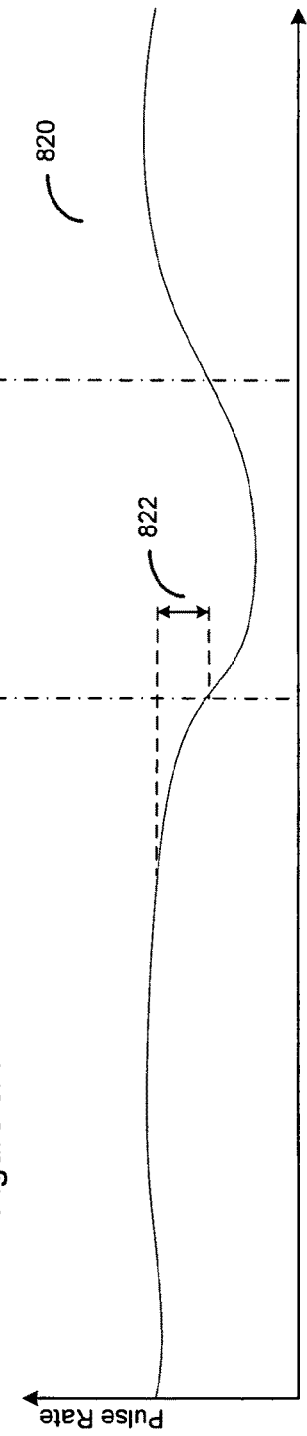
FIG. 8B illustrates a representative graph of heart rate signal used in connection with disordered breathing prediction in accordance with embodiments of the invention.
Figure 8C:
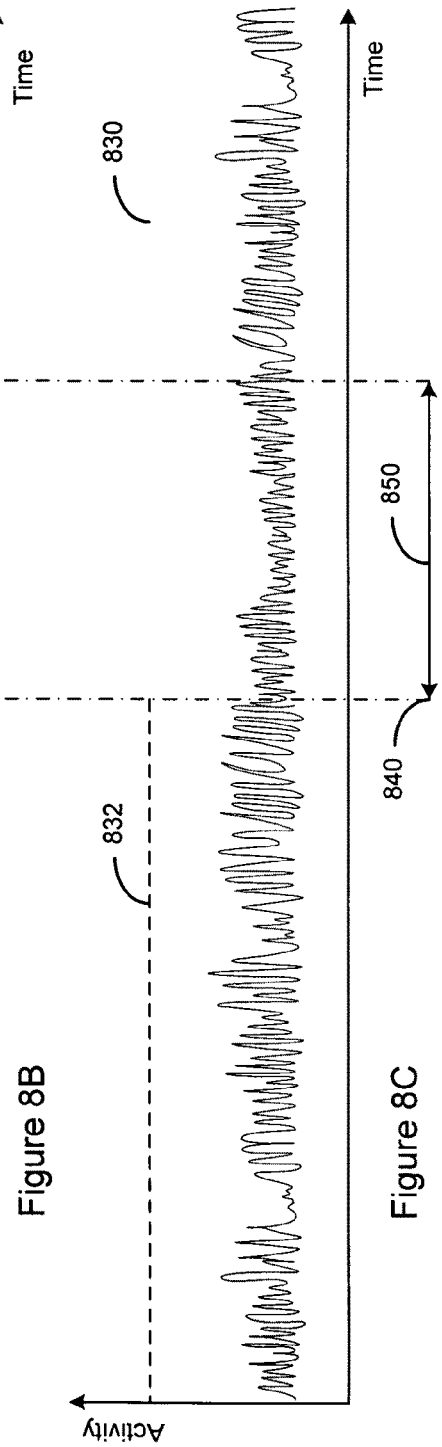
FIG. 8C illustrates a representative graph of an activity signal used in connection disordered breathing prediction in accordance with embodiments of the invention.
Figure 9:
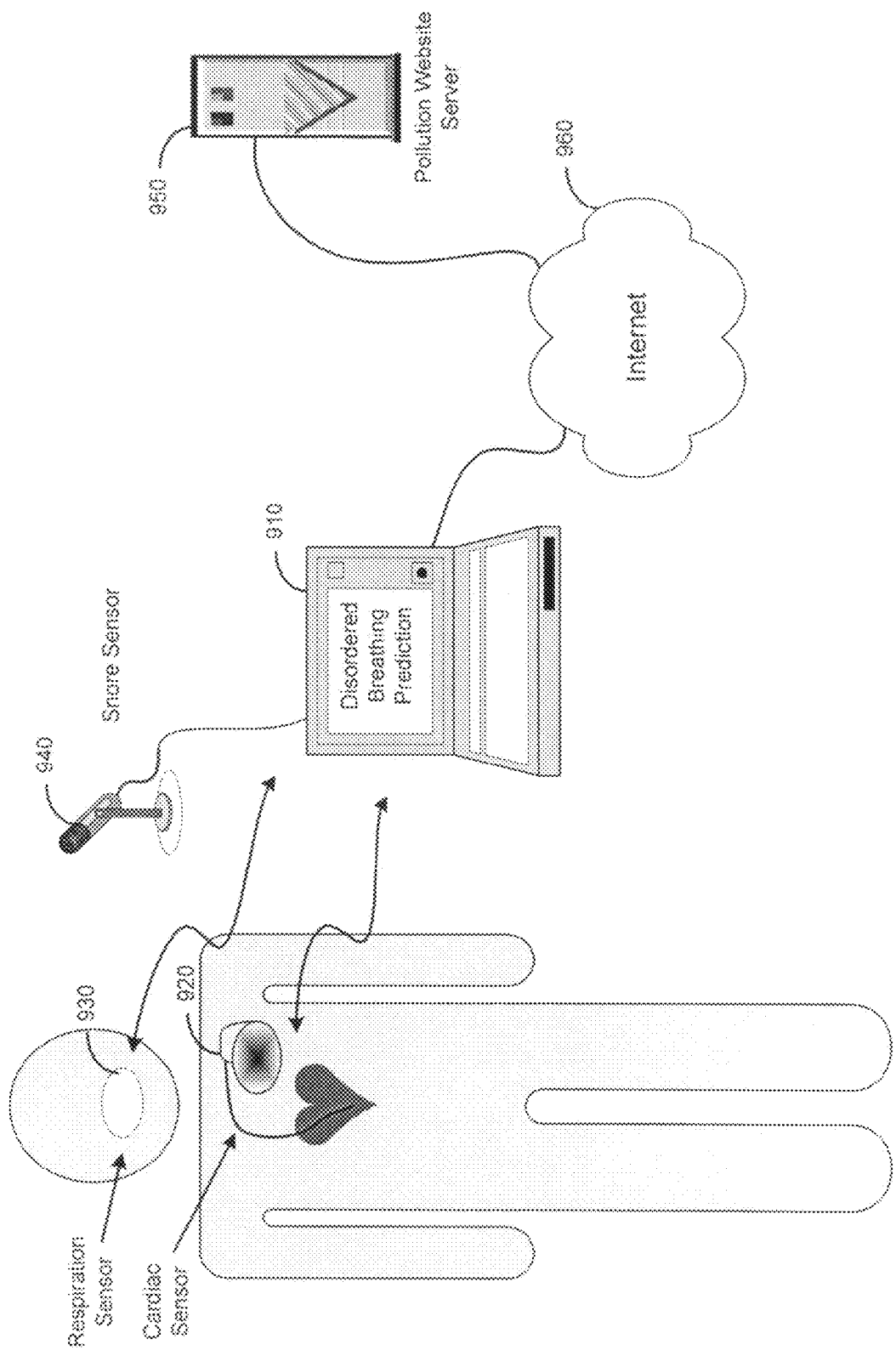
FIG. 9 is a diagram illustrating a system for predicting disordered breathing in accordance with embodiments of the invention.

FIGS. 7 through 9 illustrate systems that may be used to implement methods of disordered breathing prediction according to embodiments of the invention. FIG. 7 illustrates a system for predicting disordered breathing utilizing the cardiac rhythm management system 710 incorporating a disordered breathing prediction engine 710 as discussed in connection with FIG. 6. In addition to the previously described implanted cardiac electrodes, the cardiac rhythm management system 710 also includes an accelerometer mounted within the housing of the cardiac rhythm management system for sensing patient activity.

In the embodiment of FIG. 7, the cardiac rhythm management system 710 further includes a receiver for a proximity to bed signal that is generated by a proximity to bed beacon 720 located on or near the patient's bed 730. If the proximity to bed receiver detects a signal of sufficient strength from the proximity to bed beacon 720, then the receiver signals that the patient is in bed.

The cardiac rhythm management system 710 includes a transthoracic impedance sensor used to determine conditions associated with disordered breathing including respiration rate, respiration rate variability, tidal volume, and minute ventilation, for example. In this example, the disordered breathing prediction engine located within the cardiac rhythm management system 710 predicts disordered breathing based primarily on the patient's heart rate and tidal volume. Two additional signals, the patient's activity level and proximity to bed, are used to verify the prediction of disordered breathing.

Data associated with disordered breathing prediction may be collected by the disordered breathing prediction engine, or other components, and stored in the memory of the cardiac rhythm management system or the disordered breathing prediction engine. The data may include, for example, the number and/or types of disordered breathing episodes predicted, the number and/or types of disordered breathing episodes detected, the accuracy of the predictions made by the prediction engine, or other data useful for diagnostic or therapeutic purposes. For example, the data stored may involve counting the number of successful disordered breathing predictions made and/or counting the number of unsuccessful disordered breathing predictions made. A system for predicting disordered breathing may include a display or other output device capable of displaying information associated with the disordered breathing predictions in the form of graphics, text, or other media. Alternatively or additionally, the collected data may be transmitted to a separate device for storage, display, report generation, further analysis, or other purposes.

The methods and systems for predicting disordered breathing as illustrated by the embodiments described herein may be used in cooperation with advanced patient management systems. Advanced patient management systems allow physicians to remotely and automatically monitor patient conditions and test physiological functions, including cardiac and respiratory functions, for example. In one example of advanced patient management, an implantable cardiac rhythm management system, such as cardiac pacemaker, defibrillator, or cardiac resynchronization device, may be equipped with various telecommunications and information technologies enabling real-time data collection, diagnosis, and treatment of the patient. Advanced patient management systems may be enhanced by real-time prediction of disordered breathing and/or long term collection of disordered breathing prediction data. Systems and methods involving advanced patient management techniques are described in U.S. Pat. Nos. 6,336,903, 6,312,378, 6,270,457, and 6,398,728 which are incorporated herein by reference in their respective entireties.

Representative graphs of the patient's tidal volume 810, heart rate 820, and activity level 830 during disordered breathing prediction are illustrated in FIGS. 8A-8C. In this example, the patient's tidal volume 810 exhibits a characteristic decrease 812 just before the onset 840 of an episode of disordered breathing 850. Accordingly, a first condition threshold for disordered breathing prediction is established as a percentage drop in tidal volume. Additionally, the patient's heart rate 820 exhibits a decrease 822 that occurs substantially simultaneously with the decrease in tidal volume 812. A second condition threshold for disordered breathing detection is established as a percentage drop in heart rate.

If the system detects that the percent decrease in tidal volume and the percent decrease in heart rate exceed the established thresholds, a disordered breathing prediction is made subject to verification. The disordered breathing prediction is then verified by determining that the patient's activity signal 830, as detected by the accelerometer, is below a resting threshold 832 and that the proximity to bed receiver indicates that the patient is in bed.

Another embodiment of a disordered breathing prediction system is illustrated in the diagram of FIG. 9. In this embodiment, the prediction criteria for predicting disordered breathing are based on the patient's heart rate, respiration rate, the condition of patient snoring, and air quality.

In this embodiment, a heart rate signal is wirelessly transmitted from the cardiac rhythm management system 920 to an external disordered breathing prediction unit 910. An external respiration monitor 930 produces respiration signals and wirelessly transmits the respiration signals to the disordered breathing prediction unit 910. A snore sensor 940, which may be implemented as a microphone or accelerometer, for example, is coupled through a lead to the disordered breathing prediction unit 910 for detection of patient snoring. The disordered breathing prediction unit 910 accesses an air quality website server 950 through a network, such as the internet 960, and downloads information regarding air quality.

The examples presented herein represent a subset of many ways in which the described sensors and systems may be combined to implement disordered breathing prediction in accordance with principles of the invention. It will be appreciated that many combinations of physiological and/or environmental conditions may be detected and used to predict disordered breathing according to the methods and systems described herein.

The following commonly owned U.S. patents and Publications, some of which have been identified above, are hereby incorporated by reference in their respective entireties: 7,252,640; 7,189,204; 2005/0042589;7,720,541; 2005/0043652, and 7,680,537.

Various modifications and additions can be made to the preferred embodiments discussed above without departing from the scope of the present invention. Accordingly, the scope of the present invention should not be limited by the particular embodiments described above, but should be defined only by the claims set forth below and equivalents thereof.

What is claimed is:

1. A method of operating a medical device to predict disordered breathing in a patient, comprising:
    measuring a transthoracic impedance of the patient;
    detecting a pulmonary congestion condition of the patient based on the measured transthoracic impedance;
    comparing the detected pulmonary congestion condition to a prediction criterion; and
    predicting disordered breathing based on the comparison, wherein each of measuring, detecting, comparing and predicting is performed by the medical device.

2. The method of claim 1, wherein the detecting includes detecting a plurality of conditions associated with disordered breathing, of which the pulmonary congestion condition is one.

3. The method of claim 1, wherein the detecting includes detecting a plurality of conditions predisposing the patient to disordered breathing, of which the pulmonary congestion condition is one.

4. The method of claim 1, wherein the detected pulmonary congestion condition is one of a plurality of detected conditions, wherein the prediction criterion is included in one or more sets of prediction criteria, and wherein the comparing includes comparing the plurality of detected conditions to the one or more sets of prediction criteria.

5. The method of claim 1, wherein the predicting is performed at least in part implantably.

6. The method of claim 1, wherein each of measuring, detecting, comparing, and predicting is performed at least in part implantably.

7. The method of claim 1, wherein the detected pulmonary congestion condition is one of a plurality of detected conditions, and wherein the comparing includes (a) computing an estimated probability that disordered breathing will occur based on the detected conditions, and (b) comparing the estimated probability to a threshold probability associated with an onset of disordered breathing.

8. The method of claim 1, wherein the prediction criterion is included in one or more sets of prediction criteria, the method further comprising:

adjusting a particular set of prediction criteria based on the detected pulmonary congestion condition.

9. The method of claim 1, wherein the predicting includes predicting the disordered breathing will occur within a particular time interval.

10. A medical device operable to predict disordered breathing in a patient, comprising:

a sensor configured to sense a transthoracic impedance of the patient;

a detector system coupled to the sensor and configured to detect conditions associated with disordered breathing, the detected conditions including a pulmonary congestion condition of the patient; and a prediction engine coupled to the detector system and configured to predict disordered breathing based on the detected conditions.

11. The device of claim 10, wherein the prediction engine includes an implantable component.

12. The device of claim 10, wherein the sensor, the detector system, and the prediction engine each include an implantable component.

13. The device of claim 10, wherein the prediction engine is further configured to (a) compare the detected pulmonary congestion condition to a prediction criterion, and (b) predict the disordered breathing based on the comparison.

14. The device of claim 10, wherein the prediction engine is further configured to (a) compare the detected conditions to one or more sets of prediction criteria, and (b) predict the disordered breathing based on the comparison.

15. The device of claim 14, wherein the prediction engine is further configured to (a) compute an estimated probability that disordered breathing will occur based on the detected conditions, and (b) compare the estimated probability to a threshold probability associated with an onset of disordered breathing.

16. The device of claim 14, wherein the prediction engine is further configured to adjust a particular set of prediction criteria based on the detected pulmonary congestion condition.

17. The device of claim 14, wherein the prediction engine is configured to predict that the disordered breathing will occur within a particular time interval.

18. The device of claim 10, further comprising a data storage unit configured to store data associated with disordered breathing predictions.

19. The device of claim 18, wherein the data storage unit is configured to count a number of disordered breathing predictions.

* * * * *